United States Patent
Pon et al.

(10) Patent No.: US 7,135,564 B1
(45) Date of Patent: *Nov. 14, 2006

(54) REUSABLE SOLID SUPPORT FOR OLIGONUCLEOTIDE SYNTHESIS

(75) Inventors: Richard T. Pon, Calgary (CA); Shuyuan Yu, Calgary (CA)

(73) Assignee: University Technologies International Inc. (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/720,907

(22) PCT Filed: Jun. 30, 1999

(86) PCT No.: PCT/CA99/00600

§ 371 (c)(1),
(2), (4) Date: Jul. 10, 2001

(87) PCT Pub. No.: WO00/01711

PCT Pub. Date: Jan. 13, 2000

Related U.S. Application Data

(60) Provisional application No. 60/091,683, filed on Jul. 2, 1998.

(30) Foreign Application Priority Data

Jul. 2, 1998 (CA) .................. 2242649

(51) Int. Cl.
*C07H 21/00* (2006.01)
(52) U.S. Cl. ................ 536/25.3; 536/25.33; 536/25.34
(58) Field of Classification Search ............ 536/25.3, 536/25.33, 25.34
See application file for complete search history.

(56) References Cited

U.S. PATENT DOCUMENTS

| | | | | |
|---|---|---|---|---|
| 5,624,711 A | * | 4/1997 | Sundberg et al. | 427/261 |
| 5,736,626 A | * | 4/1998 | Mullah et al. | 536/25.3 |
| 5,770,687 A | * | 6/1998 | Hornik et al. | 530/311 |
| 5,777,077 A | * | 7/1998 | Albericio et al. | 530/335 |
| 5,798,276 A | * | 8/1998 | Haugland et al. | 436/546 |
| 5,817,751 A | * | 10/1998 | Szardenings et al. | 530/317 |
| 5,817,811 A | * | 10/1998 | Breiphol et al. | 544/264 |
| 6,015,895 A | * | 1/2000 | Pon et al. | 536/25.3 |
| 6,043,353 A | * | 3/2000 | Pon et al. | 536/25.3 |

FOREIGN PATENT DOCUMENTS

| | | | |
|---|---|---|---|
| WO | WO 92/06103 A1 | * | 4/1992 |
| WO | WO 93/07883 A1 | * | 4/1993 |
| WO | WO 97/23496 A1 | * | 7/1997 |
| WO | WO 97/23497 A1 | * | 7/1997 |

OTHER PUBLICATIONS

Pon et al. (III), "Hydroquinone-O,O'-Diacetic Acid as a More Labile Replacement for Succinic Acid Linkers in Solid-Phase Oligonucleotide Synthesis," *Tetrahedron Letters*, 38(19), 3327-3330 (May 12, 1997).*

(Continued)

*Primary Examiner*—L. E. Crane
(74) *Attorney, Agent, or Firm*—Katten Muchin Rosenman LLP

(57) ABSTRACT

A reusable linker arm for solid support oligonucleotide synthesis, the linker arm comprising formula (a) wherein Z is a linker moiety and T is an organic radical. A method for adding one or more nucleosides on the linker arm is also described

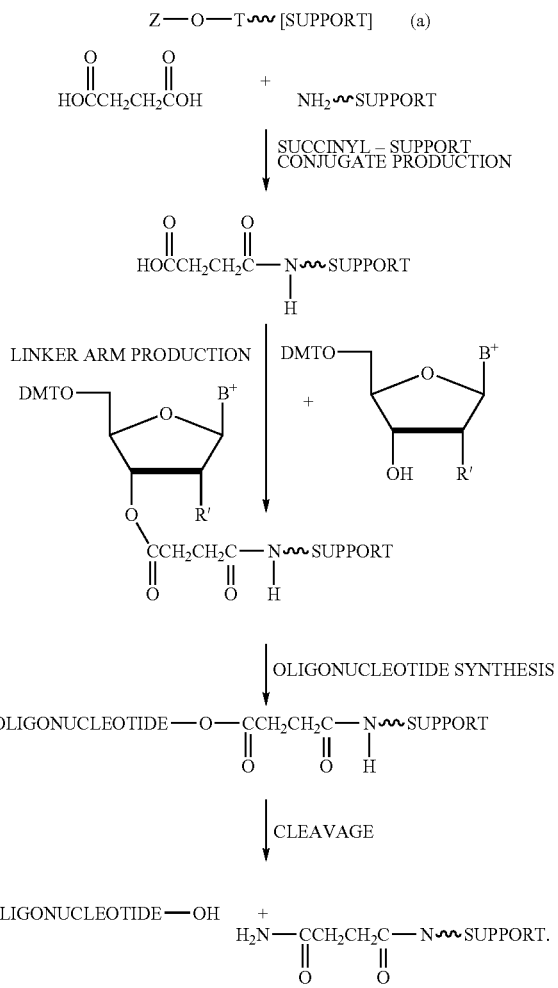

97 Claims, 3 Drawing Sheets

OTHER PUBLICATIONS

Pon et al. (IV), "Rapid Automated Derivatization of Solid-Phase Supports for Oligonucleotide Synthesis Using Uronium or Phosphonium Coupling Reagents," *Tetrahedron Letters*, 38(19), 3331-3334 (May 12, 1997).*

Pon et al. (V), "Hydroquinone-O, O'-Diacetic Acid ('Q-Linker') as a Replacement for Succinyl and Oxalyl Linker Arms in Solid Phase Oligonucleotide Synthesis," *Nucleic Acids Research*, 25(18), 3629-3635 (1997).*

I. W. James, "Linkers for Solid Phase Organic Synthesis—Tetrahedron Report No. 489," *Tetrahedron*, 55, 4855-4946 (1999).*

Tanaka et al., "[]," *Tetrahedron*, 44(14), 4331-4338 (1988); cited by applicants in prior U.S. Appl. No. 09/091,513; copy not presently available.*

* cited by examiner

A, OHS Linker Arm (Preferred example)

(General example, $R^9$ = H or protecting group, $X^3$ and $X^4$ = NH, NR, or O)

B, $C_{12}$ Linker Arm (Preferred example)

(General example, $X^5$ = NH, NR, or O)

C, BDG Linker Arm (Preferred example)

(General example, X = O, NH, or NR, R' = protecting group)

D, GLY Linker Arm (Gly-CPG)

(Preferred example)

(General example)

SEQUENCE LISTING

<160> NUMBER OF SEQ ID NOS: 1

<210> SEQ ID NO 1
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: Misc-structure
<222> LOCATION: (1) ... (20)
<223> OTHER INFORMATION: Synthetic

<400> SEQUENCE: 1
gcccaagctg gcatccgtca                                            20

REUSABLE SOLID SUPPORT FOR OLIGONUCLEOTIDE SYNTHESIS

This application is a 371 application of PCT/CA99/00600, filed Jun. 30, 1999 which claims the benefit of provisional application U.S. 60/091,683, filed Jul. 2, 1998, now abandoned.

TECHNICAL FIELD

In one of its aspects, the present invention relates to a reusable solid support for oligonucleotide synthesis. In another of its aspects, the present invention relates to a process for production of such a reusable solid support. In yet another of its aspects, the present invention relates to a process for use of such a reusable solid support.

BACKGROUND ART

The art of organic chemistry on solid supports is generally known. A useful review article on this topic may be found in "Organic Chemistry on Solid Supports" by Früchtel et al., *Angew. Chem. Int. Ed. Engl.,* 1996, 35, pgs. 17–42, the contents of which are hereby incorporated by reference.

As discussed in Früchtel et al., the art has developed automated solid-phase synthesis of polypeptides, oligonucleotides and oligosaccharaides. Of particular interest here is solid-phase synthesis of oligonucleotides. The following are useful review articles/textbooks on this topic:

Beaucage et al., *Tetrahedron,* 1992, 48, 2223;
Davis et al., *Innovation and Perspectives in Solid Phase Synthesis* (Ed.; R. Epton), Intercept, Andover, 1992, pg. 63;
Montserra et al., *Tetrahedron,* 1994, 50, 2617; and
S. L. Beaucage et al., *Tetrahedron,* 1993, 49, 6123–6194;

the contents of each of which are hereby incorporated by reference.

In the solid-phase synthesis of oligonucleotides, it is known to synthesize the oligonucleotide on an inorganic solid support bearing a succinyl linker arm—see, for example, any of the following references:

Caruthers et al., *Genetic Engineering,* Plenum Press, New York (1982), Vol. 4, pgs. 1–17;
Letsinger et al., *Genetic Engineering,* Plenum Press, New York (1985), Vol. 5, pg. 191;
Froehler et al., *Nucleic Acids Research,* 14:5399–5407 (1986); and
Matteucci et al., *Journal of American Chemical Society,* 103:3185–3186 (1981);

the contents of each of which are hereby incorporated by reference.

Typically, the succinyl linker arm has the following general formula:

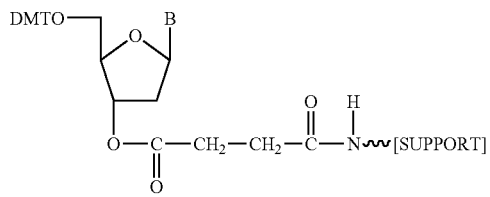

Thus, the succinyl group links the growing oligonucleotide from its terminal 3' hydroxyl group by an ester bond to a primary amine on the support, which may be, for example, conventional controlled pore glass (CPG) or silica, by an amide bond. Once the desired oligonucleotide has been synthesized, it is freed or cleaved from the succinyl linker arm hydrolyzing the ester carbonyl group. The hydrolysis agent is usually concentrated ammonium hydroxide. Typically, this reaction can take from 1–4 hours to complete. With improvements to current solid-phase oligonucleotide synthesizers, this cleavage step can represent 50% or more of the total time require to synthesize the desired oligonucleotide.

Another type of linker arm is disclosed in U.S. Pat. No. 5,112,962 [Letsinger et al. (Letsinger)], the contents of which are hereby incorporated by reference. Letsinger teaches a linker arm for solid support synthesis of oligonucleotides and oligonucleotide derivatives have the following formula:

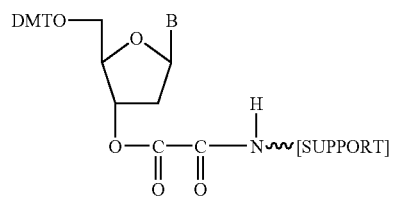

Thus, Letsinger teaches an oxalyl linker arm which purportedly release the synthesized oligonucleotide or oligonucleotide derivate in a period of 1–30 minutes in a manner that leaves the oligonucleotide fully protected. The oxalyl linker arm purportedly can be rapidly cleaved by 5% ammonium hydroxide in methanol, ammonium hydroxide, wet tertiary amine, triethylamine/alcohol, triethylamine/methanol, triethylamine/ethanol, aqueous trimethylamine and other bases. Unfortunately, the oxalyl linker arm of Letsinger suffers from its purported advantage. Specifically, the present inventors have discovered that the oxalyl linker arm of Letsinger is susceptible to significant spontaneous hydrolysis (e.g. spontaneous hydrolysis of ~10–40% per month) which renders it difficult to use in commercial operations. The oxalyl arm is also difficult to prepare because it requires using oxalyl chloride, which is highly reactive, toxic and therefore dangerous.

Regardless of the specific nature of the linker arm, it is generally accepted in the art that the linker arm is not reusable after production and cleavage of the desired oligonucleotide. Thus, conventional linker arms may be regarded as non-recyclable. This is illustrated in FIG. 1 which illustrates the conventional use of a succinyl linker arm for the production of an oligonucleotide. Thus, as illustrated, after cleavage of the desired oligonucleotide, the support is irreversibly linked to the linker compound (i.e., the succinyl moiety) and cannot be reused.

The art is in need of a linker arm for solid support oligonucleotide synthesis, which linker arm is recyclable. More specifically, the art is in need of a linker arm capable of repeated oligonucleotide synthesis/cleavage.

In published International patent application WO 97/23496 [Pon et al.], the contents of which are hereby incorporated by reference, there is reported the first recyclable linker arm. This linker arm is based on a derivatized solid support having the following formula:

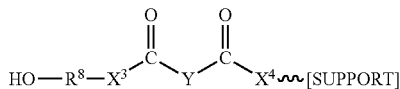

wherein: $R^8$ is selected from the group consisting of a substituted or unsubstituted $C_1$–$C_{20}$ alkyl group, a substituted or unsubstituted $C_5$–$C_{30}$ aryl group and a substituted or unsubstituted $C_5$–$C_{40}$ alkylaryl group; $X^3$ and $X^4$ are the same or different and are selected from the group consisting of —O—, —S—, —S(O)$_2$— and —N($R^{12}$)—; $R^{12}$ is selected from the group consisting of a substituted or unsubstituted $C_1$–$C_{20}$ alkyl group a substituted or unsubstituted $C_5$–$C_{30}$ aryl group and a substituted or unsubstituted $C_5$–$C_{40}$ alkylaryl group; and Y is selected from the group consisting of:
—CH$_2$—CH$_2$—; —CH$_2$—;
—CH$_2$—O—CH$_2$—; —CH$_2$—CH$_2$—CH$_2$—;
—CH═CH—; —CH═C(CH$_3$)—;
—C(CH$_3$)═C(CH$_3$)—; —CH$_2$—C(═CH$_2$)—; and
—CH$_2$—S—CH$_2$—.

While a linker arm based on the solid support described by Pon et al. is a significant advance in the art, there is still room for improvement. Specifically, the solid support described by Pon et al. has the following disadvantages.

First, prior to attachment of the linker moiety, the solid support must be derivatized by a process comprising the step of reacting together the compounds of Formulae I, II and III:

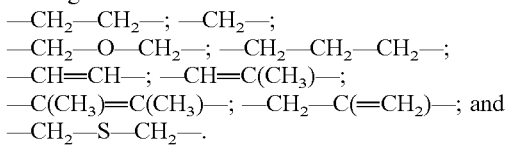

wherein $R^8$, $X^3$, $X^4$ and Y are as defined above. Practically, this involves two steps—i.e., reaction of the compound of Formula III with one of the compounds of Formulae I and II and subsequent reaction with the other of compounds of Formulae I and II. Thus, the disadvantage is additional labour required to effect a two-step derivatization of the solid support.

Second, each step of the derivatization described in the previous paragraph has the potential of incompletely derivatizing each $HX^4$-moiety on the support thereby increasing the likelihood of a heterogeneous surface. Practically, it becomes necessary to block or cap underivatized $HX^4$-moieties so that the linker moiety does interact with them. Thus, the disadvantage is additional labour and cost required to effect derivatization of the solid support.

Third, a linker arm based on the derivatized support described by Pon et al. is not as resistant to partial cleavage during regeneration as a derivatized support having a more fully saturated moiety.

In light of these disadvantages, it would be desirable to have an improved recyclable solid state support material useful in the oligonucleotide synthesis. It would be especially desirable if the the linker moiety could be attached to the support material with little or no derivatization required of the latter.

DISCLOSURE OF THE INVENTION

It is an object of the present invention to provide a novel solid support for oligonculeotide synthesis which obviates or mitigates at least one of the above-mentioned disadvantages of the prior art.

It is another object of the present invention to provide a novel process for producing the solid support.

It is an object of the present invention provide a novel linker arm for solid support oligonucleotide synthesis which obviates or mitigates at least one of the above-mentioned disadvantages of the prior art.

It is another object of the present invention to provide a novel process for producing a linker arm for solid support oligonucleotide synthesis.

Accordingly, in one of its aspects, the present invention provides a reusable linker arm for solid support oligonucleotide synthesis, the linker arm comprising the following formula:

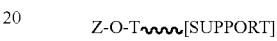

wherein Z is a linker moiety and T is an organic radical.

In another of its aspects, the present invention provides a reusable linker arm for solid support oligonucleotide synthesis, the linker arm comprising the following formula:

NUCLEOSIDE-Z-O-T∿∿[SUPPORT]

wherein Z is a linker moiety and T is an organic radical.

In yet another of its aspects, the present invention provides a process for production of a reusable linker arm for oligonucleotide synthesis having the following formula:

Z-O-T∿∿[SUPPORT]

wherein Z is a linker moiety and T is an organic radical, the process comprising the step of reacting together the compounds of Formulae I and II:

Z-OH                                    (I)

HO-T∿∿[SUPPORT]                         (II)

wherein Z and T are as defined above.

In another of its aspects, the present invention provides a process for production of a reusable linker arm for oligonucleotide synthesis having the following formula:

NUCLEOSIDE-Z-O-T∿∿[SUPPORT]

wherein Z is a linker moiety and T is an organic radical, the process comprising the step of reacting together the compound of Formulae I, II and III:

HO-Z-OH                                 (I)

HO-T∿∿[SUPPORT]                         (II)

NUCLEOSIDE-OH                           (III)

wherein Z and T are as defined above.

In yet another of its aspects, the present invention provides a process for producing an oligonucleotide having a desired sequence comprising the steps of:
(i) reacting a linker arm having the formula:

NUCLEOSIDE-Z-O-T∿∿[SUPPORT]

wherein Z is a linker moiety and T is an organic radical, with at least one oligonucleoside base until an oligonucleotide having the desired sequence is produce;

(ii) cleaving the oligonucleotide having the desired sequence to produce a free oligonucleotide have the desired sequence; and a used linker arm; and (iii) recycling the used linker arm to Step (i).

As used throughout this specification, the term "oligonucleotide" is intended to have a broad meaning and encompasses conventional oligonucleotides, backbone-modified oligonucleotides (e.g. phosphorothioate, phosphorodithioate and methyl-phophonate analogs useful as oligotherapeutic agents) and oligonucleotide derivatives such as oligonucleotide-peptide conjugates.

Throughout this specification, when reference is made to a substituted moiety, the nature of the subsitution is not specification restricted and may be selected from the group consisting of a $C_1$–$C_{20}$ alkyl groups, a $C_5$–$C_{30}$ aryl group a $C_5$–$C_{40}$ alkaryl group.

BRIEF DESCRIPTION OF THE DRAWINGS

Embodiments of the present invention will be described with reference to the accompany drawing in which.

BEST MODE FOR CARRYING OUT THE INVENTION

Initially, to facilitate an understanding of the invention, reference will be made to FIG. 1, which illustrates a conventional process for solid support oligonucleotide synthesis.

Figure 1:
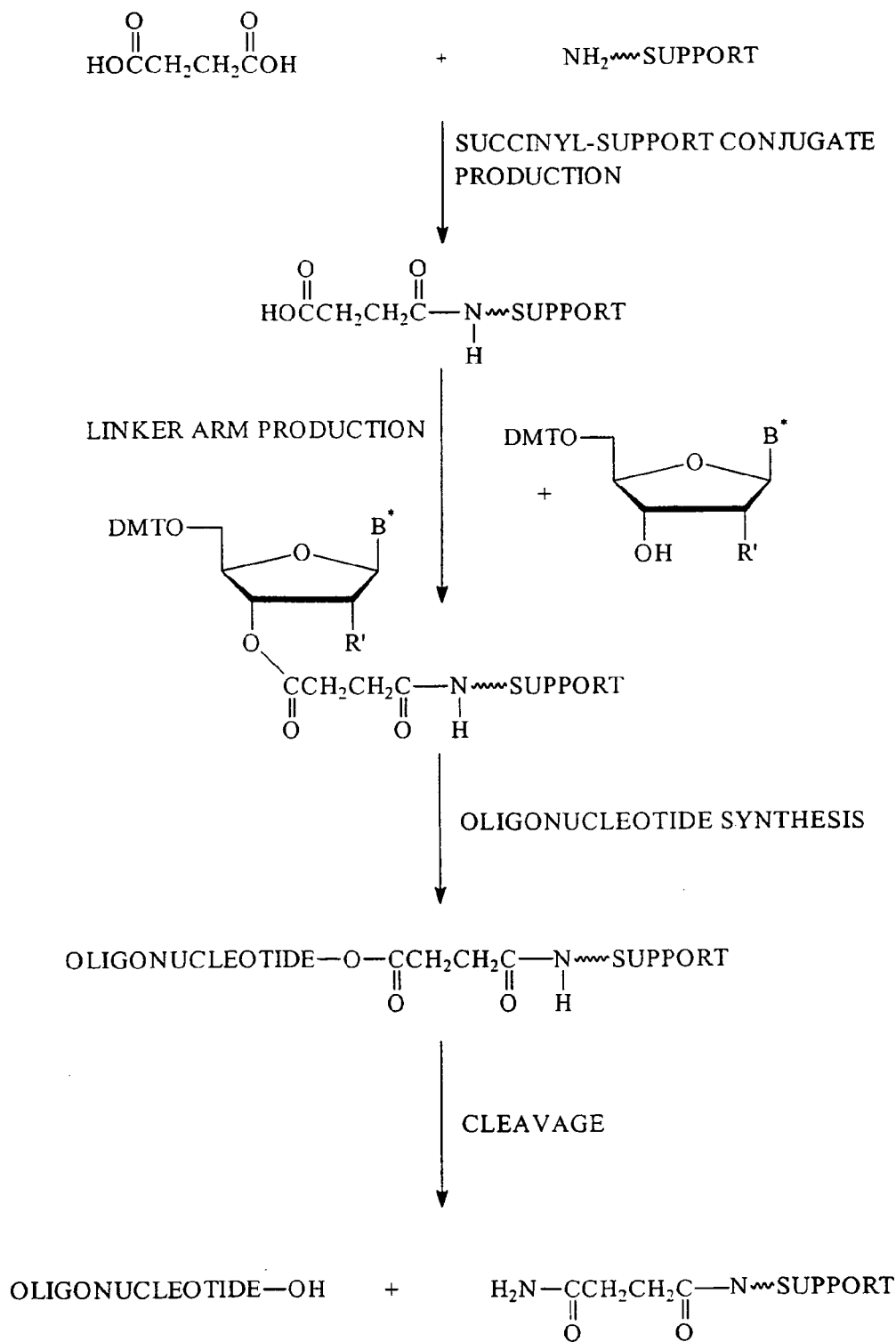
FIG. 1 illustrates a specific process pathway for conventional oligonucleotide synthesis.

Thus, the initial step of the process illustrated in FIG. 1 comprises reacting a linking compound, such as succinic acid (while succinic acid is illustrated, succinic anhydride may also be used), with a conventional amine-terminated support. The reaction results in the formation of an amide linkage between the linking compound and the support to produce succinyl-support conjugate.

Next, the succinyl-support conjugate is reacted with a desired initial nucleoside to produce a linker arm. In the illustrated nucleoside, DMT is dimethyoxytrityl, B is the nucleobase and R' is H (for deoxyribonucleosides) or OR (for ribonucleosides) wherein R is H or a conventional blocking/protecting group. The reaction results in the formation of an ester linkage between the linking compound and the desired initial nucleoside at the 3' position of the latter.

The linker arm is then used in conventional oligonucleotide synthesis (e.g. in a conventional automated synthesizer) to produce an oligonucleotide of desired sequence attached to the linker arm.

The oligonucleotide is then cleaved from the linker by hydrolysis. This serves to cleave the ester bond thereby freeing the oligonucleotide and an amine-terminated, non-reusable linker arm.

The present inventors have surprisingly and unexpectedly discovered that a support having a hydroxy-terminated functionality may be combined with a conventional linking compound to produce linker arm which may used to synthesize an oligonucleotide of desired sequence. A key feature of the invetion is that the linker arm may be regenerated or recycled after cleavage of the oligonucleotide of desired sequence. To the inventors' knowledge, this is the first discovery of a derivatized support which may be used repeatedly in oligonucleotide synthesis.

The reusable linker arm of the present invention has the following formula:

wherein Z is a linker moiety and T is an organic radical.

Preferably, T contains at least one carbon.

Preferably, T is a $C_1$–$C_{300}$ organic moiety, more preferably a $C_1$–$C_{200}$ organic moiety, most preferably a $C_1$–$C_{100}$ organic moiety.

As will be appreciated by those of skill in the art, T may be a saturated or unsaturated organic moiety. Further, T may contain one or more heteroatoms. For example, T may comprise at least one heteroatom selected from N and O.

In one preferred embodiment, the organic moiety in T comprises at least one moiety having the formula:

In another preferred embodiment, the organic moiety in T comprises at least one moiety having the formula:

—N(H)—.

In yet another preferred embodiment, the organic moiety in T comprises at least one moiety having the formula:

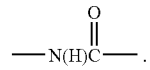

In yet another preferred embodiment, the organic moiety in T comprises at least one moiety having the formula:

—C—O—C—.

In yet another preferred embodiment, the organic moiety in T comprises at least one moiety having the formula:

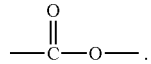

Further, those of skill in the art will recognize that the organic moiety in T may be unsubstituted or substituted. For examples, the organic moiety of T may be substituted by at least one moiety selected from the group comprising a $C_1$–$C_{40}$ alkyl group, a $C_5$–$C_{40}$ aryl group, a $C_1$–$C_{40}$ alkoxy croup, a $C_1$–$C_{40}$ ester group, a $C_1$–$C_{40}$ hydroxy group, a $C_1$–$C_{40}$ acrylate group and a $C_5$–$C_{40}$ alkylaryl group.

In one preferred embodiment, T has the formula:

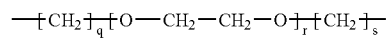

wherein q and s are the same or different and each is an integer having a value of 0–40 and r is an integer having a value of 1–200. In this embodiment, it is further preferred that q and s are the same or different and each is an integer having a value of 1–20 and r is an integer having a value of 1–150.

In another preferred embodiment, T has the formula:

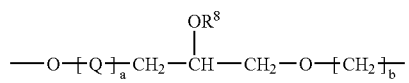

wherein a is 0 or 1, Q is an organic moiety, $R^8$ is hydrogen or a protecting group and b is an integer having a value of 0–40. In this embodiment, a may be 0 and $R^8$ may be hydrogen. Further, a may be 1 and $R^8$ may be a protecting group. Non-limiting examples of protecting groups may be selected from the group comprising acetyl, chloroacetyl, methoxyacetyl, t-butyl phenoxyacetyl, phenoxyacetyl, trityl, methoxytrityl, dimethoxytrityl (DMT), dialkylphosphite, pivalyl-isobutyloxycarbonyl, t-butyldimethylsilyl, phenoxyacetal, 9-phenylxanthen-9-yl (pixyl), tetrahydropyranyl, methoxytetrahydropyranyl, methoxymethyl, benzyloxymethyl, methoxyethoxymethyl, methylthiomethyl, dialkylphosphate, levulinyl, dimethylphenylsilyl, trimethylsilyl, isopropyl-dimethylsilyl, diisopropylmethylsilyl, diethylisopropylsilyl, triisopropylsilyl, acetyl, benzoyl, pivaloyl, trifluoroacetyl, allyl, benzyl, o-nitrobenzyl, o-hydroxystyryldimethylsilyl, 2-oxo-1,2-diphenylethyl, allyloxycarbonyl, monomethoxymethyl, nitroveratryloxycarbonyl, dimethoxybenzoin, dimethoxybenzoin carbonate, methylnitropiperonyl carbonate, fluorenyl-methoxycarbonyl, 2-phenylsulfonylethoxycarbony, fluorophenyl-methoxypiperidinyl and mixtures thereof.

In this embodiment, Q may be a moiety having the formula:

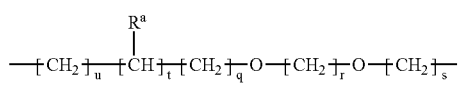

wherein q, r, s, t and u are the same or different and each is an integer having a value of 0–40 and $R^a$ is selected from the group comprising hydrogen, hydroxyl, a $C_1$–$C_{40}$ alkyl group, a $C_5$–$C_{40}$ aryl group, a $C_1$–$C_{40}$ alkoxy group, a $C_1$–$C_{40}$ ester group, a $C_1$–$C_{40}$ hydroxy group, a $C_2$–$C_{40}$ acrylate group and a $C_5$–$C_{40}$ alkylaryl group. Preferably, s is 0, q, r and u are the same or different and each is an integer having a value of 1–10, t is an integer of 1–5 and $R^a$ is hydroxyl.

In yet another preferred embodiment, T has the formula:

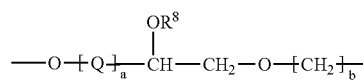

wherein a is 0 or 1, Q is an organic moiety, $R^8$ is selected from the group comprising hydrogen, hydroxyl, a $C_1$–$C_{40}$ alkyl group, a $C_1$–$C_{40}$ aryl group, a $C_1$–$C_{40}$ alkoxy group, a $C_1$–$C_{40}$ ester group, a $C_1$–$C_{40}$ hydroxy group, a $C_1$–$C_{40}$ acrylate group and a $C_5$–$C_{40}$ alkylaryl group, and b is an integer having a value of 0–40. Preferably, Q is a $C_1$–$C_{100}$ organic moiety. As will be appreciated by those of skill in the art, Q may be a saturated organic moiety or an unsaturated organic moiety.

It is preferred that Q is a $C_1$–$C_{100}$ organic moiety comprising at least one heteroatom selected from N and O.

In one preferred embodiment, the organic moiety Q comprises at least one moiety having the formula:

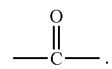

In another preferred embodiment, the organic moiety Q comprises at least one moiety having the formula:

N(H)—.

In yet another embodiment, the organic moiety Q comprises at least one moiety having the formula:

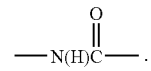

In yet another embodiment, the organic moiety Q comprises at least one moiety having the formula:

—C—O—C—.

In yet another embodiment, the organic moiety comprises at least one moiety having the formula:

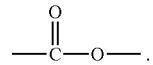

As will be appreciated by those of skill in art, the organic moiety Q may unsubstituted or substituted. For example, the organic moiety Q may be substituted by at least one moiety selected from the group comprising a $C_1$–$C_{40}$ alkyl group, a $C_1$–$C_{40}$ aryl group, a $C_1$–$C_{40}$ alkoxy group, a $C_1$–$C_{40}$ ester group, a $C_1$–$C_{40}$ hydroxy group, a $C_1$–$C_{40}$ acrylate group and a $C_1$–$C_{40}$ alkylaryl group.

In one preferred embodiment, Q has the formula:

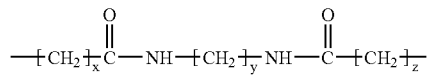

wherein each of x, y and z is an integer having a value of 1–40.

In the above formula for the present linker arm, Z is a linker moiety. As will be discussed below, Z is derived from a linker compound have the general formula HO-Z-OH (Formula I below). The nature of the linker compound is not particularly restricted.

In one preferred embodiment, linker moiety Z has the formula:

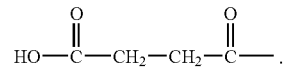

As will be apparent to those of skill in the art, this linker moiety may be derived from succinic acid or succinic anhydride.

In another preferred embodiment, linker moiety Z has the following formula:

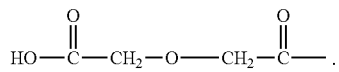

As will be apparent to those of skill in the art, this linker moiety may be derived from diglycolic acid or diglycolic anhydride.

In yet another preferred embodiment, linker moiety Z has the following formula:

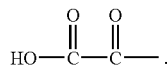

As will be apparent to those of skill in the art, this linker moiety may be derived from oxalic acid or oxalyl chloride.

In yet another, and most, preferred embodiment, linker moiety Z has the following formula:

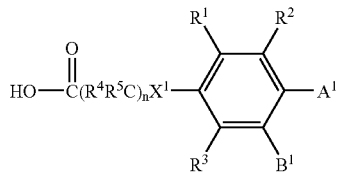

wherein: $R^1$, $R^2$ and $R^3$ are the same or different and are selected from the group consisting of hydrogen, halide, a substituted or unsubstituted $C_1$–$C_{20}$ alkyl group, a substituted or unsubstituted $C_5$–$C_{30}$ aryl group and a substituted or unsubstituted $C_5$–$C_{40}$ alkylaryl group; $R^4$ and $R^5$ are the same or different and are selected from the group consisting of hydrogen, a substituted or unsubstituted $C_1$–$C_{20}$ alkyl group, a substituted or unsubstituted $C_5$–$C_{30}$ aryl group and a substituted or unsubstituted $C_5$–$C_{40}$ alkylaryl group; $X^1$ is selected from the group consisting of —O—, —C(O)—, —S—, —S(O)$_2$— and —N(R)—; R is selected hydrogen, a substituted or unsubstituted $C_1$–$C_{20}$ alkyl group, a substituted or unsubstituted $C_5$–$C_{30}$ aryl group and a substituted or unsubstituted $C_5$–$C_{40}$ alkylaryl group; n is 0, 1 or 2; and one of $A^1$ and $B^1$ is selected from the group consisting of hydrogen, halide, a substituted or unsubstituted $C_1$–$C_{20}$ alkyl group, a substituted or unsubstituted $C_5$–$C_{30}$ aryl group and a substituted or unsubstituted $C_5$–$C_{40}$ alkylaryl group, and the other of $A^1$ and $B^1$ has the formula:

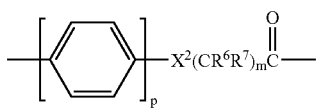

wherein p is 0 or 1, $X^2$ is selected from the group consisting of —O—, —S—, —C(O)—, —S(O)$_2$— and —N(R)—, R is selected from the group comprising hydrogen, a substituted or unsubstituted $C_1$–$C_{20}$ alkyl group, a substituted or unsubstituted $C_5$–$C_{30}$ aryl group and a substituted or unsubstituted $C_5$–$C_{40}$ alkylaryl group, $R^6$ and $R^7$ are the same or different and are selected from the group consisting of hydrogen, a substituted or unsubstituted $C_1$–$C_{20}$ alkyl group, a substituted or unsubstituted $C_5$–$C_{30}$ aryl group and a substituted or unsubstituted $C_5$–$C_{40}$ alkylaryl group, and m is 0, 1 or 2. In this embodiment, $B^1$ preferably is selected from the group consisting of hydrogen, halide, a substituted or unsubstituted $C_1$–$C_{20}$ alkyl group, a substituted or unsubstituted $C_5$–$C_{30}$ aryl group and a substituted or unsubstituted $C_5$–$C_{40}$ alkylaryl group. Preferably, at least one, more preferably each, of R, $R^4$, $R^5$, $R^6$ and $R^7$ is hydrogen and preferably at least, more preferably both, of m and n are 1. It is further preferred that each of $R^1$, $R^2$ and $R^3$ is hydrogen and that $X^1$ and $X^2$ are both —O—. Thus, in this embodiment, the most preferred form of linker moiety Z is derived from hydroquinone-O,O'-diacetic acid.

In yet another preferred embodiment, linker moiety Z has the following formula:

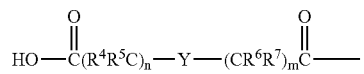

wherein $R^4$, $R^5$, $R^6$ and $R^7$ are the same or different and are selected from the group consisting of hydrogen, a substituted or unsubstituted $C_1$–$C_{20}$ alkyl group, a substituted or unsubstituted $C_5$–$C_{30}$ aryl group and a substituted or unsubstituted $C_5$–$C_{40}$ alkylaryl group, Y is selected from the group consisting of O, S, SO$_2$ and O—((CH$_2$)$_1$—O)$_q$, 1 is an integer less than or equal to 60, q is an integer in the range of 1–1000, n and m are the same or different and are 1 or 2, with the proviso that, when Y is O, at least one of n and m is 2. Preferably, 1 is an integer in the range of 1–10, and q is an integer in the range of 1–000. In this embodiment, the most preferred form of linker moiety Z is derived from thiodiglycolic acid (i.e. $R^4$=$R^5$=$R^6$=$R^7$=H, n=m=1 and Y=S).

The SUPPORT in the above formula is a conventional solid support. The nature of the solid support is not particularly restricted and is within the purview of a person skilled in the art. Thus, the solid support may be an inorganic substance. Non-limiting examples of suitable inorganic substances may be selected from the group consisting of silica, porous glass, aluminosilicates, borosilicates, metal oxides (e.g. aluminum oxide, iron oxide, nickel oxide) and clay containing one or more of these. Alternatively, the solid support may be an organic substance such as a cross-linked polymer. Non-limiting examples of a suitable cross-linked polymer may be selected from the group consisting of polyamide, polyether, polystyrene and mixtures thereof. The preferred solid support for use herein is conventional and may be selected from controlled pore glass bead or polystyrene beads. Further, the support may be either in particle form (e.g., beads), three-dimensional slabs (e.g., polymeric inserts and foams) or in a flat two-dimensional like format (e.g., plastic sheets, glass chips, silicon wafers, etc.). The material used for the support may also be soluble in certain solvents (e.g., liquid-phase supports), but can be precipitated or crystallized from other solvents.

The reusable linker of formula:

(again, Z is a linker moiety and T is an organic radical), may then be reacted with a conventional nucleoside-linker compound to produce another linker arm according to the present invention. This other linker arm has the following formula:

NUCLEOSIDE-Z-O-T∼∼∼[SUPPORT]

wherein Z is a linker moiety and T is an organic radical. The discussion herein above with respect to Z and T applies equally here. Preferably, in the above formula, NUCLEOSIDE is a moiety selected from one of the following formulae:

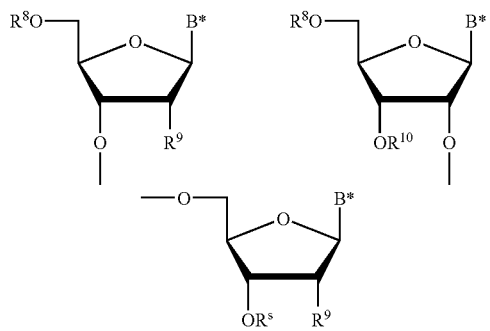

wherein $R^8$ and $R^{10}$ are the same or different and are hydrogen or a protecting group, $R^9$ is hydrogen (for deoxyribonucleosides or DNA) or —$OR^{11}$ (for ribonucleosides or RNA) wherein $R^{11}$ is hydrogen or a protecting group, and B* a nucleic acid base. Thus, in the case of RNA, there are two hydroxyl groups which may be protected. Also, the linker can be attached to either the 5'-, 3'- or (if ribose) 2'-hydroxyl positions. Indeed, for RNA sequences, it makes little difference whether the ester linker formed between the nucleoside and the linker compound is at the 2'- or 3'-hydroxyl position of the nucleoside. Thus, those of skill in the art will recognize that the nucleoside may be protected or blocked at the various of its hydroxyl moieties.

Non-limiting examples of useful protecting groups may be selected from the group consisting of acetyl, chloroacetyl, methoxyacetyl, t-butyl phenoxyacetyl, phenoxyacetyl, trityl, methoxytrityl, dimethoxytrityl (DMT), dialkylphosphite, pivalyl-isobutyloxycarbonyl, t-butyldimethylsilyl, phenoxyacetal, 9-phenylxanthen-9-yl (pixyl), tetrahydropyranyl, methoxytetrahydropyranyl, methoxymethyl, benzyloxymethyl, methoxyethoxymethyl, methylthiomethyl, dialkylphosphate, levulinyl, dimethylphenylsilyl, trimethylsilyl, isopropyldimethylsilyl, diisopropylmethylsilyl, diethylisopropylsilyl, triisopropylsilyl, acetyl, benzoyl, pivaloyl, trifluoroacetyl, allyl, benzyl, o-nitrobenzyl, o-hydroxystyryldimethylsilyl, 2-oxo-1,2-diphenylethyl, allyloxycarbonyl, monomethoxymethyl, nitroveratryloxycarbonyl, dimethoxybenzoin, dimethoxybenzoin carbonate, methylnitropiperonyl carbonate, fluorenyl-methoxycarbonyl, 2-phenylsulfonylethoxycarbony, fluorophenyl-methoxypiperidinyl and the like.

As is known in the art, the main prerequisite for the protecting group used on the 5'-hydroxyl position is its ability to be selectively removed without causing cleavage of the linker arm. Thus, the preferred protecting group for desired 5'-hydroxyl position(s) is the acid labile dimethoxytrityl group. The main prerequisite for protecting groups on other hydroxyl positions, is stability to the conditions used for removal of the above protecting group. These latter protecting groups may be removed by the same conditions used to cleave the linker (discussed below) or separate conditions. The preferred protecting groups for these positions are trialkylsilyl (i.e. t-butyldimethylsilyl) or acetyl. Additional information may be obtained from the following references:

1. T. W. Greene and P. G. M. Nuts, "Protecting Groups in Organic Synthesis", Second Edition (1991), John Wiley and Sons, Inc., NY;
2. M. Schelhaas and H. Waldman, "Protecting Group Strategies in Organic Synthesis", Angew. Chemie Int. Ed. Engl. 35, 2056–2083 (1996);
3. M. J. Gait, ed., "Oligonucleotide Synthesis A Practical Approach", IRL Press, Oxford (1984);
4. S. A. Narang, ed., "Synthesis and Applications of DNA and RNA", Academic Press, Inc., Orlando (1987); and
5. S. Agrawal, ed., "Methods in Molecular Biology, Vol. 20: Protocols for Oligonucleotides and Analogs", Humana Press, Totowa, N.J. (1993);

the contents of each of which are hereby incorporated by reference, for a discussion of other possible hydroxyl protecting groups.

The manner by which the desired nucleoside may be protected is conventional and within the purview of a person skilled in the art. See, for example U.S. Pat. No. 3,400,190 (Melby), U.S. Pat. No. 4,458,066 (Caruthers et al.).

A preferred method for production of deoxyribonucleosides in the context of the present invention is to use a nucleoside with a 5'-dimethoxytrityl protecting group and an appropriate exocyclic amino protecting group, e.g., $N^6$-benzoyl-5'-dimethoxytrityl-2'-deoxyadenosine, $N^4$-benzoyl-5'-dimethoxytrityl-2'-deoxycytidine, 5'-dimethoxytrityl-$N^2$-isobutyryl-2'-deoxyguanosine, or 5'-dimethoxytritylthymidine.

A preferred method for production of ribonucleosides in the context of the present invention is to use a 5'-dimethoxytrityl protected nucleoside, with appropriate exocyclic amino protection, and no protecting groups on either of the 2'- or 3'-hydroxyl positions. The linker can then react with either one of the two adjacent hydroxyl groups (it doesn't matter which) to give a mixture of 2'- and 3'-linkages. The unreacted hydroxyl groups may then be acetylated by treatment of the immobilized nucleoside with acetic anhydride. Alternatively, ribonucleosides which have a 5'-dimethoxytrityl group, appropriate exocyclic amino group protection, and either a 3'-hydroxyl protecting group or a mixture of 2'- and 3'-protecting groups can be used. The 3'-protected compounds are generally unwanted isomers which are simultaneously produced when the 2'-hydroxyl position is protected and having little other use.

The reusable linker arm having the formula:

Z-O-T∼∼∼[SUPPORT]

may be produced by a process comprising the step of reacting together the compound of Formulae I and II:

Z-OH  (I)

HO-T∼∼∼[SUPPORT]  (II)

wherein Z and T are as defined above.

The reusable linker arm having the formula:

NUCLEOSIDE-Z-O-T∼∼∼[SUPPORT]

comprises the step of reacting together the compounds of Formulae I, II and III:

HO-Z-OH  (I)

HO-T~~~[SUPPORT]  (II)

NUCLEOSIDE-OH  (III)

wherein Z and T are as defined above.

The compounds of Formulae I and II or of Formulae I, II and III (depending on which version of the present linker arm is being produced) are preferably reacted in the presence of an activating agent. As used throughout this specification, the term "activating group" is intended to have a broad meaning and is intended to encompass electrophilic reagents capable of activating a carboxyl moiety (e.g., on the linking compound of Formula II) by attachment of a leaving group to the acyl carbon of the carboxl moiety—see, for example, M. Bodanszky, "Principles of Peptide Synthesis", Second Edition, Springer-Verlag, Berlin (1993). Thus, the activating agent should be capable of initiating at least one of the following: (a) formation of a reactive acylating agent (this is an example of a derivate) from the carboxyl moeiy in a separate step or steps, followed by immediate treatment with the amino component (in this case, for example, an amino-terminated support) to form an amide linkage or a hydroxy component (in this case a hydroxy-terminated support or a hydroxyl group on the desired nucleoside) to form an ester linkage; (b) formation of an isolable acylating agent, separately, optionally with purification prior to treatment with the amino or hydroxy component as discussed in (a); and (c) formation of an acylating intermediate in the presence of the amino/hydroxy component, by the addition of an activating agent to a mixture of the two components. Thus, each of (a), (b) and (c) are applicable to the formation of both carboxylic esters and amides and all three routes can be used to attach nucleosides to supports.

For example, the Letsinger method, which first reacts oxalyl chloride with triazole, and then adds a nucleoside to the resulting oxalyl triazolide is an example of route (a). Conversion of the carboxylic acid group into an "active" ester using either p-nitrophenol, or di-, tri-, tetra-, or pentachlorinated or fluorinated phenols, or N-hydrosuccinimide are common examples of route (b). Route (c) has been the most commonly used method in recent years and both the carbodiimide reagents (dicyclohexylcarbodiimide, 1-(3-dimethylaminopropyl)-ethylcarbodiimide, and diisopropylcarbodiimide) and uronium reagents (O-(7-azabenzotriazol-1-yl)-1,1,3,3-tetramethyluronium hexafluorophosphate (HATU), 2-(1H-benzotriazol-1-yl)-1,1,3,3-tetramethyluronium hexafluorophosphate, (HBTU)) may be used in this approach.

In a preferred embodiment, in addition to an activating reagent, the reaction of the compounds of Formulae I, II and III is conducted in the presence of a nucleophilic catalyst or additive (typically 4-dimethylamino pyridine (DMAP), 1-hydroxybenzotriazole (HOBt), or 1-hydroxy-7-azabenzotriazole (HOAt)) to speed up the reaction and a tertiary amine base (typically triethylamine, pyridine, or diisopropylethylamine) to ionize the carboxylic acid group.

Thus, those of skill in the art will recognize that the precise nature of the activation agent is not particularly restricted provided, of course, that the activated carboxylic acid group is capable of initiating formation of the ester or amide linkage, as appropriate, and the activating reagent does not have any deleterious effect on the desired nucleoside.

Thus, activation of the carboxylic acid by conversion into an acid chloride; an active ester (i.e., nitrophenyl, nitrophenylthio, trichlorophenyl, trifluorophenyl, pentachlorophenyl, pentafluorophenyl, or 3-hydroxy-2,3-dihydro-4-oxobenzotriazine esters); an active hydroxylamine ester (i.e., N-hydroxyphthalimide or N-hydroxysuccinimide); acid anhydride; or mixed anhydride will produce derivates which will form the desired linkage, and thus, these strategies are encompassed herein.

Non-limiting examples of activating agents may be selected from the group consisting of arylsulfonyl chlorides (e.g., benzenesulfonyl chloride (BS—Cl), mesitylenesulfonyl chloride (MS—Cl), triisopropylsulfonylchloride (TPS—Cl)); active arylsulfonyl esters (i.e., imidazole, triazole, nitrotriazole, or tetrazole esters of BS—Cl, MS—Cl or TPS—Cl); 2-ethoxy-1-(ethoxycarbonyl)-1,2-dihydroquinoline (EEDQ); acyl carbonates; 1,1'-(carbonyldioxy)dibenzotriazoles; chlorotrimethyl-silane; carbodiimides (i.e., dicyclohexylcarbodiimide (DCC), 1-(3-dimethylaminopropyl)-ethylcarbodiimide (DEC), diisopropylcarbodiimide (DIC)) either alone or in combination with auxiliary nucleophiles (i.e., 1-hydroxybenzotriazole (HOBt), 1-hydroxy-7-azabenzotriazole (HOAt), N-hydroxysuccinimide (HOSu), or 3-hydroxy-3,4-dihydro-1,2,3-benzotriazin-4-one (HOObt)) and/or catalysts (i.e., 4-dimethylaminopyridine (DMAP) or N-methylimidazole (NMI)); or uronium salts (i.e., tetramethyluronium chloride (TMU—Cl), 2-(1H-benzotriazol-1-yl)-1,1,3,3-tetramethyluronium hexafluorophosphate (HBTU), 2-(1H-benzotriazol-1-yl)-1,1,3,3-tetramethyluronium tetrafluoroborate (TBTU), 2-succinimido-1,1,3,3-tetramethyluronium tetrafluoroborate (TSTU), 2-(3,4-dihydro-4-oxo-1,2,3-benzotriazin-3-yl)-1,1,3,3-tetramethyluronium tetrafluoroborate (TDBTU), 2-(2-oxo-1(2H)-pyridyl-1,1,3,3-tetramethyluronium tetrafluoroborate (TPTU), 2-(5-norbornene-2,3-dicarboximido)-1,1,3,3-tetramethyluronium tetrafluoroborate (TNTU), O-(7-azabenzotriazol-1-yl)-1,3-dimethyl-1,3-dimethyleneuronium hexa-fluorophosphate (HAMDU), O-(7-azabenzotriazol-1-yl)-1,3-dimethyl-1,3-tri-methyleneuronium hexafluorophosphate (HAMTU), O-(7-azabenzotriazol-1-yl)-1,1,3,3-bis(pentamethylene)uronium hexafluorophosphate (HAPipU), O-(7-azabenzotriazol-1-yl)-1,1,3,3-bis(tetramethylene)uronium hexafluorophosphate (HAPyU), O-(7-azabenzotriazol-1-yl)-1,1,3,3-tetramethyluronium hexafluorophosphate (HATU)) either alone or in combination with auxiliary nucleophiles (i.e., 1-hydroxybenzotriazole (HOBt), 1-hydroxy-7-azabenzotriazole (HOAt), N-hydroxysuccinimide (HOSu), or 3-hydroxy-3,4-dihydro-1,2,3-benzotriazin-4-one (HOObt)) and/or catalysts (e.g. 4-dimethylaminopyridine (DMAP) or N-methylimidazole (NMI)) or phosphonium salts (e.g. benzotriazol-1-yl-oxytris(dimethylamino)phosphonium hexafluorophosphate (BOP), benzotriazole-1-yl-oxytrispyrrolidinophosphonium hexafluorophosphate (PyBOP), 2-(benzotriazol-1-yl)oxy-1,3-dimethylimidazolidinium hexafluorophosphate (BOI), bromo tris(pyrrolidino)phosphonium hexafluorophosphate (PyBroP), 7-azabenzotriazol-1-yloxytris-(dimethylamino)phosphonium hexafluorophosphate (AOP), and 7-azabenzotriazol-1-yloxytris(pyrrolidino)phosphonium hexafluorophosphate (PyAOP)) either alone or in combination with auxiliary nucleophiles and/or catalysts (discussed above) will also produce the desired linkage.

Other examples of suitable activating reagents may be found in any of the following references:

M. Bodanszky, "Principles of Peptide Synthesis", Second Edition, Springer-Verlag, Berlin (1993);

J. Jones, "Amino Acid and Peptide Synthesis", Oxford University Press, Oxford (1992);

G Grant, "Synthetic Peptides: A Users Guide", W. H. Freeman & Co., NY (1992);

E. Haslam, Tetrahedron, 36, pg. 2409, (1980); and

M. A. Ogliaruso and J. F. Wolfe, "Synthesis of Carboxylic Acids, Esters and Their Derivatives", John Wiley & Sons, Chicester (1991);

the contents of each of which are hereby incorporated by reference.

In producing the present linker arm, the order of reaction is not particularly restricted. Thus, in one embodiment (this is the preferred embodiment), the compounds of Formulae I and III are initially reacted to form a conjugate which is reacted with the compound of Formula II. In another embodiment, the compounds of Formulae I and II are initially reacted to form a conjugate which is reacted with the compound of Formula III.

The addition of compounds of Formulae I and III to Formula II, usually will not result in the quantitative conversion of each immobilized hydroxyl group into a derivatized ligand. Therefore, it is preferred that unreacted hydroxyl groups on the surface of the support be protected (capped) by reaction with a capping reagent. This will mitigate the free hydroxyl group participating in subsequent oligonucleotide chain extension reactions, resulting in defect sequences lacking the terminal nucleoside. Preferably, the capping reagent should be reversible so that the capping agent can be removed to regenerate the hydroxyl sites prior to the next round of support derivatization. Capping of the unreacted sites is conventional and can be performed by reaction with an activated carboxylic acid or anhydride to form an ester, or by addition of a protecting group, as described hereinabove. Thus, for example, t-butylphenoxyacetic anhydride, methoxyacetic anhydride or preferably chloroacetic anhydride, combined with 2,6-lutidine and N-methylimidazole in THF solution are useful examples of capping reagents.

Figure 2:
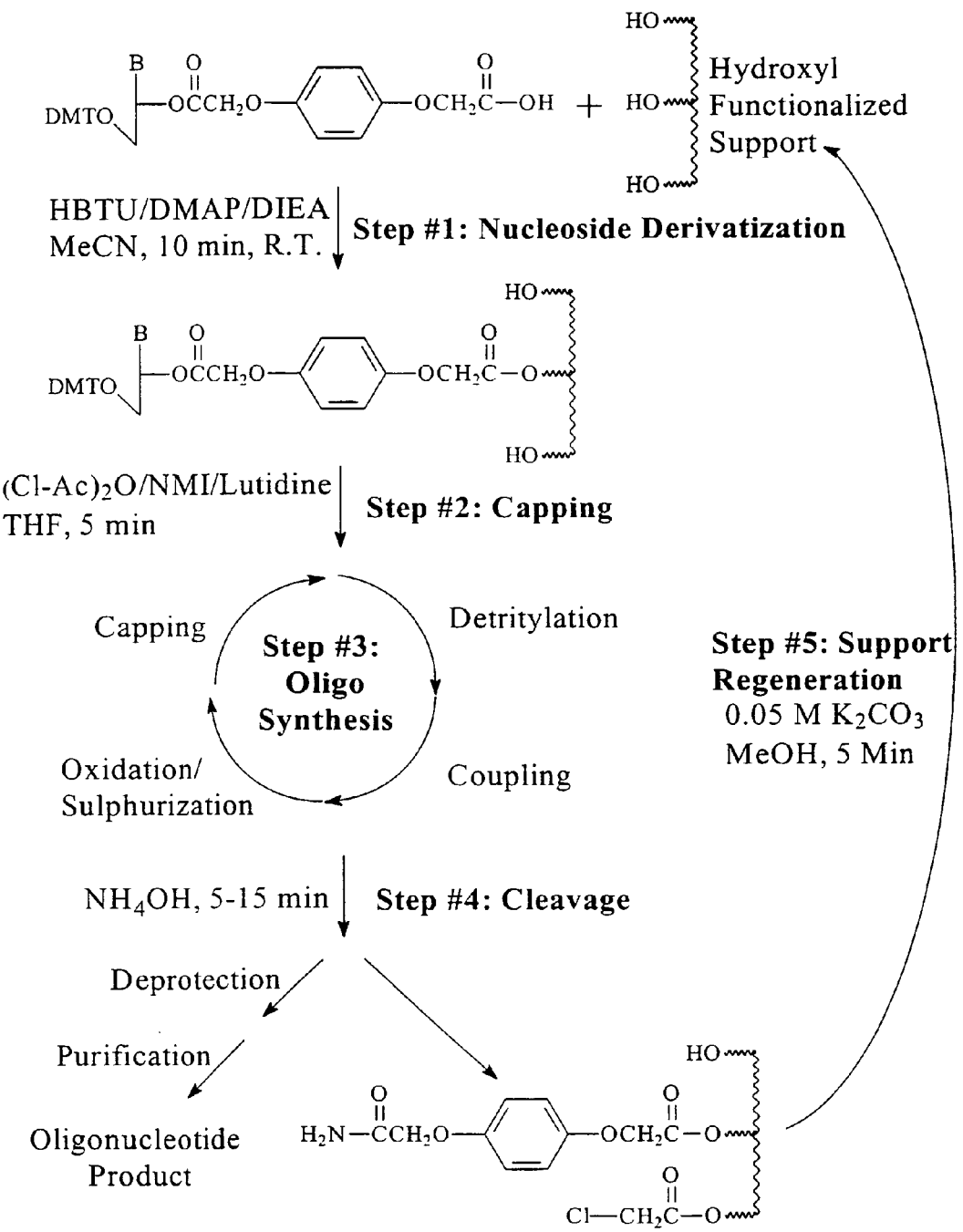
FIGS. 2 and 3 illustrate specific preferred embodiments of the present invention.

With reference to FIG. 2 there is illustrated a preferred pathway illustrating the use of the present linker arm in a recycled/regenerated manner. In FIG. 2, DMT refers to dimethoxytrityl and B refers to a nucleobase as described hereinabove. As will be apparent to those of skill in the art, the support is recycled after oligonucleotide cleavage and support regeneration to a point in the reaction scheme where it may again be coupled with the HQPD-nucleoside conjugate for further oligonucleotide synthesis.

With further reference to "Oligo Synthesis" (Step #3) in FIG. 2, once the present linker arm has been produced, it may be used in the conventional manner to synthesize an oligonucleotide—see, for example, U.S. Pat. No. 5,112,962 (Letsinger). Once the oligonucleotide has been synthesized, it may be cleaved from the solid support to yield the free oligonucleotide and the support may then be regenerated—see Step #4 of FIG. 2.

The cleavage step comprises hydrolysis at the point of attachment of the initial nucleoside to the linking compound. The regeneration of the support involves the removal of two moieties: (i) the removal of the structure represented by Formula I (above) from Formula II (above), which occurs simultaneously with the release of the oligonucleotide product, and (ii) the removal of the moiety used to protect (cap) unreacted hydroxyl sites of Formula II (above) on the support. Removal of these two moieties can occur simultaneously or separately to regenerate the support. Simultaneous removal of both moieties using only a single reagent is simpler but care should be taken to use reagents which will not deleteriously affect the oligonucleotide product. A two-step regeneration involving the removal of the oligonucleotide using one reagent (typically ammonium hydroxide) and then treatment of the support with a second reagent (which may be faster but otherwise damaging to the oligonucleotide product thereby necessitating use of a two-step regeneration) allows flexibility in the choice of capping and regeneration reagents.

The reagent used to effect cleavage is not particularly restricted and is within the purview of a person skilled in the art. Preferably, the reagent is a base mild enough not to damage the oligonucleotide product but sufficiently strong to effect rapid cleavage. Non-limiting examples of suitable reagents for this purpose may be selected from the group consisting of ammonium hydroxide, ammonium hydroxide/methanol, ammonia/methanol, ammonium hydroxide/methylamine, potassium carbonate/methanol, t-butylamine, ethylenediamine, methylamine, dimethylamine, trimethylamine/water and the like. Cleavage may also be performed under neutral conditions using fluoride ion (i.e. 1M tetrabutylammonium fluoride/THF or triethylamine trihydrofluoride). The reagent used to remove the capping reagent from unreacted sites may consist of the above reagents or other stronger bases such as sodium or potassium hydroxide. In our preferred embodiment, ammonium hydroxide can be used to cleave the oligonucleotide product from the support, remove the HQPD linker arm, and cleave chloroacetyl protected hydroxyl groups in a single regeneration step. The preferred temperature for the cleavage and regeneration is room temperature, but higher or lower temperatures can be employed, subject to the limitations of the apparatus used.

Figure 3:
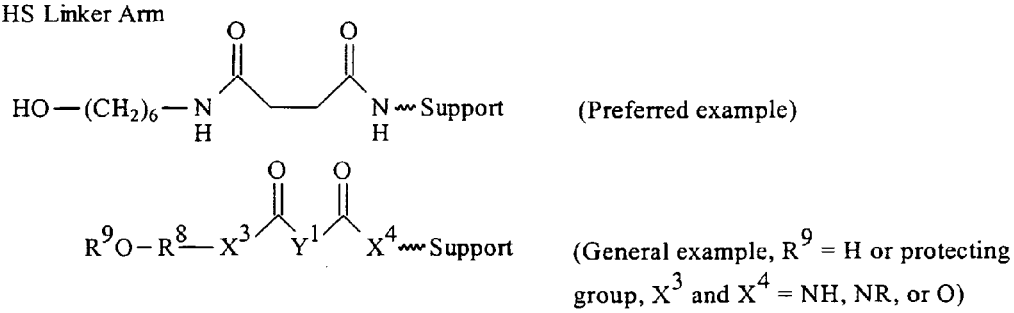
Figure 3:
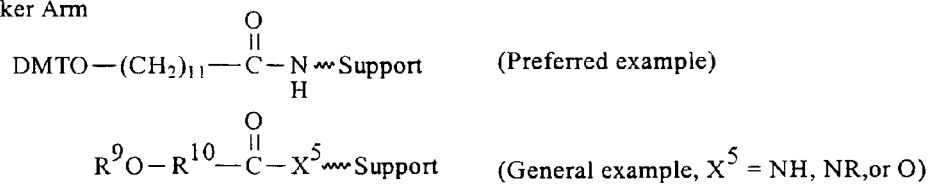
Figure 3:
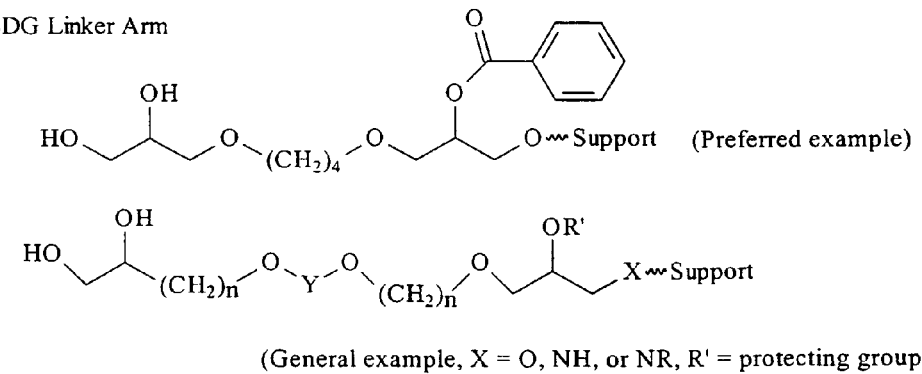
Figure 3:
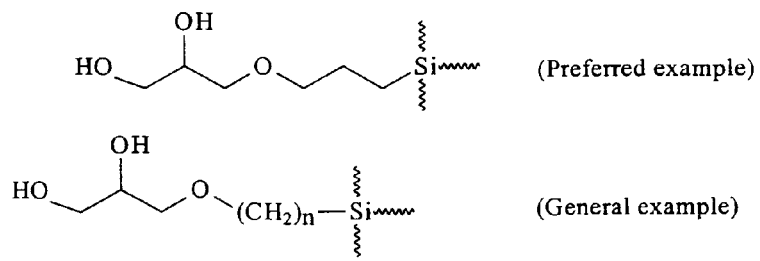

With reference to FIG. 3, there are illustrated specific preferred examples of hydroxyl reusable linker arms falling within the scope of the present invention.

Embodiments of the invention will be illustrated in the following Examples which should not be construed as limiting the scope of the invention. In the Examples, the following materials were used:

1. Long chain alkylamine (LCAA) or glycerol (Gly) derivatized controlled pore glass (CPG) beads (120/200 mesh) were obtained from CPG Inc (Lincoln Park, N.J.);

2. Toyopearl AF-amino-650M and HW65F supports were obtained from TosoHaas (Montgomeryville, Pa.);

3. Other supports were obtained from the manufacturers listed in Tables 1 and 2;

4. HQPD. Hydroquinone-O,O'-diacetic acid, commercially available from Lancaster Synthesis Ltd. (Lancashire, England);

5. Ammonium hydroxide solutions (28–30%) and solvents were obtained from VWR Canlab (Edmonton, Alberta, Canada);

6. Capping solutions were formulated as either Cap A (acetic anhydride/2,6-lutidine/THF in a volume ratio of 1:1:8) and Cap B (N-methylimidazole and THF in a volume ratio of 16:84) or Cap A (chloroacetic anhydride and THF, 17% by weight) and Cap B (2,6-lutidine and N-methylimidazole in THF in a volume ratio of 12:16:72);

7. Anhydrous pyridine and acetonitrile, distilled from $CaH_2$;

8. DIEA, diisopropylethylamine, reagent grade;

9. MeCN, acetonitrile, low water DNA synthesis grade;

10. DMAP, 4-dimethylaminopyridine, reagent grade;

11. DEC, 1-(3-dimethylaminopropyl)-ethylcarbodiimide, reagent grade;

12. Sulfurizing reagent, Beaucage thiolating reagent, from Pharmacia Biotech, was used as a 0.05M solution in acetonitrile; and 13. HBTU, 2-(1H-benzotriazol-1-yl)-1,1,3,3-tetramethyluronium hexafluoro-phosphate, reagent grade;

In the following Examples the amount of nucleoside (loading) on the insoluble supports was determined by spectrophotometric trityl analysis. In this procedure, a sample of support (4–5 mg) was accurately weighed directly into a 10 mL volumetric flask. A solution of dichloroacetic acid in 1,2-dichloroethane in a volume ration of 5:95 was then added to fill the flask. The contents were then thoroughly mixed and the absorbance of the orange coloured solution was measured at 503 nm using a Philips UV/Vis spectrophotometer. The nucleoside loading (in µmol/g of CPG) was then calculated as:

Loading=$(A_{503} \times Vol \times 1000)/(Wt \times 76)$ wherein $A_{503}$=absorbance at 503 nm, Vol=solution volume in mL, and Wt=amount of CPG tested in mg. The accuracy of the trityl determination was approximately ±2–3%.

EXAMPLE 1

Synthesis of Nucleoside-3'-O-Hoda Hemiesters

5'-Dimethoxytrityl-N-protected deoxyribonucleoside (10 mmol), hydroquinone-O,O'-diacetic acid (15 mmol, 3.39 g), 4-dimethylaminopyridine (1 mmol, 122 mg), and 1-(3-dimethylaminopropyl)-3-ethylcarbodiimide hydrochloride (15 mmol, 2.88 g) were combined in a 100 mL round bottom flask equipped with a magnetic stir bar. Triethylamine (0.8 mL) and anhydrous pyridine (50 mL) were added to the flask and the contents were stirred at room temperature overnight.

The reaction was checked by TLC (5% methanol/chloroform). If more than a trace of starting nucleoside was visible, more 1-(3-dimethylaminopropyl)-3-ethylcarbodiimide hydrochloride (2–5 mmol) was added to the reaction and stirring was continued for another day. When TLC showed complete disappearance of the starting nucleoside, the solution was concentrated by evaporation until a thick oil was formed. The oil was redissolved in chloroform (~200 mL) and transfer to a separatory funnel. The chloroform solution was washed with aqueous sodium bicarbonate (~100 mL×2) and then water (~100 mL×3). The funnel was slowly inverted to mix the two phases. The chloroform phase was collected and the aqueous phase was discarded. If an inseparable emulsion was formed, then either centrifugation (for small volumes) or (for large volumes) precipitation by addition of hexanes followed by filtration and redissolving the sticky precipitate back into chloroform can be performed.

The chloroform solution was added to anhydrous magnesium sulfate and mixed to remove residual moisture from the solution. The magnesium sulfate was filtered off, the filtrated was washed with a small amount of chloroform and then the chloroform solution was evaporated to dryness. A light brown foam, containing a mixture of diester and nucleoside hemiester sodium salt was formed and solidified.

The hemiester sodium salt was converted into a more soluble pyridinium salt by dissolving the foam in pyridine (~50–100 mL) and then adding AG 50W-X4H$^+$ cation exchange resin (2 eq.). The mixture was stirred for approximately 5 minutes and then the ion exchange resin was filtered off. The pyridine solution was evaporated to dryness. A light brown foam formed and solidified. The sold was dried under vacuum overnight to remove excess pyridine.

EXAMPLE 2

Preparation of 12-Dimethoxytrityl-Hydroxydo-Decanoic Acid Derivatized Supports

This example describes the synthesis of a $C_{12}$ linker arm within the scope of the present invention and how it can be used to convert commercially available amino-derivatized supports into reusable hydroxyl-derivatized supports.

12-Hydroxydodecanoic acid (9.25 mmol) was coevaporated to dryness with pyridine (3×). Then pyridine (~40 mL) and dimethoxytrityl chloride (10.2 mmol) were added. After stirring overnight, the solution was concentrated (to 10 mL), diluted with $CHCl_3$ (50 mL), washed with aq. $NH_4HCO_3$ (3×) and water (2×). The crude material was then purified on a silica gel column by elution with a 1% TEA/$CHCl_3$-4% MeOH/1% TEA/$CHCl_3$ gradient. The prodcut yield was 6.7 mmol (72%) of 12-dimethoxytrityl-hydroxydodecanoic acid as a brown oil.

An amino functionalized support (0.5 g), 12-dimethoxytritylhydroxy-dodecanoic acid (0.2 mmol), 4-dimethylaminopyridine (0.1 mmol), 1-(3-dimethylaminopropyl)-3-ethylcarbodiimide hydrochloride (0.6 mmol), triethylamine (0.1 mL), and pyridine (7 mL) were shaken at room temperature (16 h). The support was filtered off, washed, and dried. Linker loading was determined by trityl analysis and the results are provided in Table 1. Unreacted amino and hydroxyl groups on the derivatized support (if present) were then acetylated by treating the support with equal volumes 1 M acetic anhydride/2,6-lutidine/THF (Cap A) and 2M N-methylimidazole/THF (Cap B) reagents for 3 hours. The support was then filtered off, washed, and dried.

TABLE 1

Loading Results Using 12-Dimethoxytrityl-hydroxydodecanoic Acid Linker Arm

| Experiment | Support | Linker arm loading (µmol/g) |
|---|---|---|
| 1 | Pharmacia HL-30 amino primer support | 216 |
| 2 | Long chain alkylamine CPG | 87 |
| 3 | Amino Tentagel, Millipore | 107 |
| 4 | Toyopearl AF-amino-650M | 217 |
| 5 | Aminoethyl polystyrene, Hamilton | 73 |
| 6 | Aminomethyl polystyrene, Applied Biosystems | 28 |

EXAMPLE 3

Derivatization of Toyopearl HW-65F Support with 1,4-Butanediol Diglycidyl Ether

This Example describes how hydroxyl surface groups on commercially available Toyopearl HW65 supports are extended with a butane diglycidyl linker to create a reusable support.

Toyopearl HW-65F vinyl alcohol/methacrylic acid copolymer was obtained as a slurry in 500 ml 20% ethanol/water. This slurry was evaporated to dryness to yield of 90 g of dry support. The hydroxyl content of the dry support was determined, in triplicate, by derivatization with dimethoxytrityl chloride/tetrabutylammonium perchlorate and trityl analysis, to be 1,095 µmol/g.

The dry HW-65F support (25 g), 1.0 M aqueous NaOH solution containing 1 mg/mL $NaBH_4$ (100 mL) and 1,4- butanediol diglycidyl ether (75 mL) were shaken at room temperature (3.5 h). The support was filtered off and washed with water, acetonitrile, and then chloroform. After drying, DMT derivatization and analysis (M. P. Reddy and P. J. Voelker, 1988, Int. J. Peptide Protein Res. 31, 345–348,) of a sample indicated 902 μmol/g of remaining hydroxyl groups. Therefore, the epoxide loading was estimated to be 193 μmol/g.

The epoxide derivatized support (25 g), benzoic anhydride (51 g), 4-dimethylaminopyridine (6.6 g) and anhydrous pyridine (180 mL) were shaken at room temperature (overnight) to benzoylate unreacted hydroxyl groups. The support was filtered off, washed (methanol, then chloroform), and dried. DMT derivatization and analysis indicated that the residual hydroxyl group loading had decreased to only 5 μmol/g.

The benzoylated support (25 g), THF (140 mL), and 2.9 N aqueous $HClO_4$ (16.6 mL, 48 mmol) were shaken at room temperature (13 h). Trityl derivatization and analysis of an aliquot showed an hydroxyl loading of 98 μmol/g. Additional 2.9 N $HClO_4$ (34 mL) was added and shaking continued for another 3 h. The support was filtered off, washed, and dried and a final trityl derivatization and analysis indicated an hydroxyl loading of 103 μmol/g.

EXAMPLE 4

Synthesis of Oligonucleotide Phosphorothioates and Support Recycling Using Chloroacetic Anhydride Capping This Example provides experiments which illustrate the suitability of a variety of different supports for repetitive oligonucleotide synthesis.

The following reagents were installed on a Perkin-Elmer/Applied Biosystems 394 4-column, 8-base position DNA synthesizer:
Ports #1–4: $dA^{Bz}$, $dG^{iBu}$, $dC^{Bz}$, and T phosphoramidites (0.2 M solutions).
Port #7: 0.15 M 5'-dimethoxytrity-$N^6$-benzoyl-2'-deoxyadenosine-3'-O-hydro-quinone-O,O'-diacetyl hemiester pyridinium salt and 0.15 M diisopropylethylamine in anhydrous acetonitrile.
Port #8: 0.15 M HBTU and 0.15M DMAP in anhydrous acetonitrile.
Port #9: 0.45 M Tetrazole/acetonitrile.
Port #10: 28% Ammonium hydroxide.
Port #11: 1 M Chloroacetic anhydride in THF (Cap A reagent).
Port #12: 1 M 2,6-Lutidine and 2 M N-methylimidazole in THF (Cap B reagent).
Port #14: 5% (v/v) Dichloroacetic acid/1,2-dichloroethane.
Port # 15: 0.05 M Beaucage reagent in acetonitrile.

Up to four synthesis columns, each containing one of the supports listed in Table 2, were installed on the synthesizer and, if necessary, manually detritylated to deblock the hydroxyl linker arm.

The synthesizer was then programmed to automatically execute the following steps:
1: A "Begin" procedure consisting of a column wash, nucleoside coupling to the support by simultaneous addition (4.0 sec) of nucleoside hemiester (port #7) and coupling reagent (port #8) and a 600 sec wait, column wash, capping of unreacted hydroxyl sites (Cap A+B reagents, 300 sec), column wash, and priming of ports #1, 2, 3, 4, and 9.
2: Synthesis of the 20-base phosphorothioate oligonucleotide sequence dGCCCAAGCTGGCATCCGTCA (trityl-off) (Sequence ID No. 1).
3: A 15 minute ammonium hydroxide hydrolysis step to cleave the oligonucleotide from the support.

After completion of the ammonium hydroxide hydrolysis, the columns were removed from the synthesizer, manually treated with 0.05 M potassium carbonate/methanol solution (5 min), rinsed with methanol, dried by aspiration (5 min), re-installed on the synthesizer, and rinsed with anhydrous acetonitrile. The automated synthesis was then repeated (i.e., Steps 1, 2, and 3 above) using the same synthesis column a total of twelve times.

The amount of trityl color released after the first detritylation step was collected and quantitated to determine the amount of nucleoside added to the support—the results are reported in Table 3. The released oligonucleotide solution was deprotected (55° C. 16 h), evaporated to removed ammonia, and quantitated by UV at 260 nm—the results are reported in Table 4. The correct identity of the products, obtained from each of the results shown Table 4, was verified by electrophoresis and comparison to authentic material. Furthermore, no unusual impurities, attributable to the support recycling were present. These results confirmed that each of the nine supports used in this experiment could be reused and in several cases satisfactory results (comparable to new supports) were obtained, even after six or more uses.

EXAMPLE 5

Synthesis of Oligonucleotide Phosphorothioates and Support Recycling Using Methoxyacetic Anhydride Capping This Example illustrates the use of methoxyacetic anhydride as the capping reagent instead of chloroacetic anhydride used in the previous Examples.

The automated DNA synthesizer was set-up with reagents, as described in Example 4, with the exception of the Cap A and B reagents, which were as follows:
Port #10: 0.5 M Methoxyacetic anhydride and 0.5 M 2,6-lutidine in acetonitrile (Cap A).
Port #12: 1 M N-Methylimidazole in acetonitrile (Cap B).

The automated nucleoside derivatization, oligonucleotide synthesis, and support recycling procedure was then performed using the supports listed in Table 5 and the procedure described in Example 4. However, because of the greater stability of the methoxyacetyl group, the manual column regeneration step with 0.05M potassium carbonate/methanol was increased from 5 min to 15 min.

The amount of trityl color released after the first detritylation step was collected and quantitated to determine the amount of nucleoside added to the support—the results are reported in Table 6. The released oligonucleotide solution was deprotected (55° C., 16 h), evaporated to removed ammonia, and quantitated by UV at 260 nm—the results are reported in Table 7. The composition of the products obtained in Table 7 was examined by gel electrophoresis and the expected products were obtained in each case. This indicated that methoxyacetic anhydride could also be used as a satisfactory capping reagent during the support recycling.

TABLE 2

Supports Used For Phosphorothioate Synthesis and Support Recycling

| Experiment | Support | Linker Arm | Amount used (mg) |
|---|---|---|---|
| 1 | Long chain alkylamine CPG | Hydroxyhexylsuccinyldiamide | 16.2 |
| 2 | Long chain alkylamine CPG | Hydroxydodecanoic acid | 21.1 |
| 3 | Glycerol CPG | | 13.3 |
| 4 | Toyopearl AF-amino-650M | Hydroxydodecanoic acid | 15 |
| 5 | Aminoethyl polystyrene, Hamilton | Hydroxydodecanoic acid | 21.5 |
| 6 | Aminomethyl polystyrene, Applied Biosystems | Hydroxydodecanoic acid | 34.1 |
| 7 | Pharmacia hydroxyl primer support* | Butanediol diglycidyl | 14.5 |
| 8 | Toyopearl HW65F | Butanediol diglycidyl | 15.4 |
| 9 | Hydroxyethyl polymethacrylate/polystyrene, Hamilton | | 27.3 |

*proprietary material supplied by Pharmacia

TABLE 3

Nucleoside loading obtained after repetitive synthesis on the same support

Synthesis # and First Nucleoside Loading Level (µmol/g)

| Experiment | 1 | 2 | 3 | 4 | 5 | 6 | 7 | 8 | 9 | 10 | 11 | 12 |
|---|---|---|---|---|---|---|---|---|---|---|---|---|
| 1 | 74 | 62 | 61 | 65 | 56 | 55 | 54 | 60 | 58 | 60 | 51 | 49 |
| 2 | 57 | 58 | 54 | 56 | 54 | 54 | 54 | 62 | 51 | 49 | 56 | 46 |
| 3 | 72 | 68 | 65 | 67 | 64 | 64 | 62 | 61 | 60 | 57 | 55 | 54 |
| 4 | 96 | 119 | 130 | 130 | 126 | 123 | 65 | 60 | 46 | 34 | 25 | 17 |
| 5 | 75 | 79 | 76 | 76 | 70 | 57 | 47 | 40 | 43 | 60 | 46 | 40 |
| 6 | 30 | 35 | 35 | 37 | 38 | 35 | 35 | 36 | 31 | 33 | 37 | 33 |
| 7 | 155 | 111 | 107 | 97 | 122 | 115 | 95 | 122 | 87 | 110 | 101 | 89 |
| 8 | 107 | 110 | 116 | 113 | 111 | 104 | 102 | 87 | 76 | 92 | 71 | 66 |
| 9 | 34 | 41 | 47 | 48 | 48 | 53 | 49 | 50 | 45 | 62 | 51 | 67 |

TABLE 4

Amount of Crude Oligonucleotide Produced From Repetitive Syntheses on the Same Support Synthesis # and amount of crude product produced ($A_{260}$ units)

| Experiment | 1 | 2 | 3 | 4 | 5 | 6 | 7 | 8 | 9 | 10 | 11 | 12 |
|---|---|---|---|---|---|---|---|---|---|---|---|---|
| 1 | 7530 | 7590 | 7530 | 7650 | 6790 | 6850 | 5740 | 5930 | 4750 | 3640 | 2780 | 2350 |
| 2 | 7630 | 7680 | 6590 | 6970 | 6680 | 6680 | 6110 | 5170 | 3460 | 2420 | 2700 | 1850 |
| 3 | 8350 | 7740 | 8270 | 7970 | 8120 | 8120 | 7440 | 7370 | 6690 | 6170 | 5190 | 4660 |
| 4 | 12200 | 11500 | 12600 | 11700 | 11600 | 11800 | 9880 | 6710 | 5850 | 4750 | 3540 | 2550 |
| 5 | 8010 | 8340 | 7990 | 7960 | 7810 | 6720 | 5690 | 3900 | 3280 | 3780 | 2550 | 2050 |
| 6 | 3610 | 4300 | 4220 | 4540 | 4830 | 4560 | 4630 | 4620 | 4300 | 3730 | 3390 | 2750 |
| 7 | 9300 | 8190 | 7460 | 7620 | 8550 | 7390 | 5900 | 4900 | 2280 | 4180 | 2430 | 1750 |
| 8 | 11520 | 11100 | 10600 | 11400 | 11500 | 11400 | 9980 | n.d. | n.d. | 8390 | 5060 | 6270 |
| 9 | 2360 | 3260 | 4520 | 4630 | 5290 | 6420 | 6610 | n.d. | n.d. | 8570 | 6420 | 6830 |

TABLE 5

Supports Used For Oligonucleotide Phosphorothioate Synthesis and Support Recycling

| Experiment | Support | Linker Arm | Amount used (mg) |
|---|---|---|---|
| 1 | Glycerol CPG | | 14.5 |
| 2 | Toyopearl HW65F | Butanediol diglycidyl | 14.6 |

TABLE 6

Nucleoside Loading Obtained After Repetitive Synthesis on the Same Support

| | Synthesis # and first nucleoside loading (μmol/g) | | | | | | | | | | | |
|---|---|---|---|---|---|---|---|---|---|---|---|---|
| Experiment | 1 | 2 | 3 | 4 | 5 | 6 | 7 | 8 | 9 | 10 | 11 | 12 |
| 1 | 83 | 82 | 71 | 75 | 61 | 69 | 63 | 64 | 58 | 56 | 48 | 42 |
| 2 | 93 | 105 | 115 | 115 | 105 | 114 | 117 | 120 | 110 | 113 | 96 | 67 |

TABLE 7

Amount of Crude Oligonucleotide Produced From Repetitive Syntheses on the Same Support

| | Synthesis # and amount of crude product produced ($A_{260}$ units) | | | | | | | | | | | |
|---|---|---|---|---|---|---|---|---|---|---|---|---|
| Experiment | 1 | 2 | 3 | 4 | 5 | 6 | 7 | 8 | 9 | 10 | 11 | 12 |
| 1 | 8100 | 7750 | 7570 | 7850 | 6910 | 7500 | 7440 | 7400 | 6870 | 6810 | 6210 | 5220 |
| 2 | 8480 | 9820 | 10200 | 10900 | 9490 | 10200 | 10300 | 10700 | 10000 | 9190 | 8450 | 6170 |

---

What is claimed is:

1. A reusable linker arm for solid support oligonucleotide synthesis, the linker arm consisting of the following formula:

Z-O-T∿∿∿[SUPPORT]

wherein Z is selected from the group consisting of:
$HO_2C-CH_2-CH_2-(C=O)-$;
$HO_2C-CH_2-O-CH_2-(C=O)-$;
$HO_2C-(C=O)-$; and

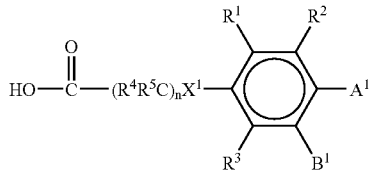

wherein: $R^1$, $R^2$ and $R^3$ are the same or different and are selected from the group consisting of hydrogen, halide, a substituted or unsubstituted $C_1-C_{20}$ alkyl group, an substituted or unsubstituted $C_5-C_{30}$ aryl group and a substituted or unsubstituted $C_5-C_{40}$ alkylaryl group;

$R^4$ and $R^5$ are the same or different and are selected from the group consisting of hydrogen, a substituted or unsubstituted $C_1-C_{20}$ alkyl group, an substituted or unsubstituted $C_5-C_{30}$ aryl group and a substituted or unsubstituted $C_5-C_{40}$ alkylaryl group;

$X^1$ is selected from the group consisting of —O—, —S—, —C(O)—, —S(O)$_2$—, and —N(R)—;

R is selected from the group consisting of hydrogen, a substituted or unsubstituted $C_1-C_{20}$ alkyl group, an substituted or unsubstituted $C_5-C_{30}$ aryl group and a substituted or unsubstituted $C_5-C_{40}$ alkylaryl group;

n is 0, 1 or 2;

and one of $A^1$ and $B^1$ is selected from the group consisting of hydrogen, halide, a substituted or unsubstituted $C_1-C_{20}$ alkyl group, an substituted or unsubstituted $C_5-C_{30}$ aryl group and a substituted or unsubstituted $C_5-C_{40}$ alkylaryl group and the other of $A^1$ and $B^1$ has the formula:

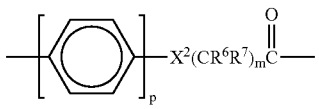

wherein p is 0 or 1;

$X^2$ is selected from the group consisting of —O—, —S—, —C(O)—, —S(O)$_2$—, and —N(R)—;

R is selected from the group consisting of hydrogen, a substituted or unsubstituted $C_1-C_{20}$ alkyl group, an substituted or unsubstituted $C_5-C_{30}$ aryl group and a substituted or unsubstituted $C_5-C_{40}$ alkylaryl group;

$R^6$ and $R^7$ are the same or different and are selected from the group consisting of hydrogen, a substituted or unsubstituted $C_1-C_{20}$ alkyl group, an substituted or unsubstituted $C_5-C_{30}$ aryl group and a substituted or unsubstituted $C_5-C_{40}$ alkylaryl group;

and T has the formula:

$-[CH_2]_q-[O-CH_2-CH_2-O]_r-[CH_2]_s-$ wherein q and s are the same or different and each is an integer having a value of 0–40 and r is an integer having a value of 1–200 or T has the formula:

$-[Q]_a-CH_2-CH(R^a)-CH_2-O-[CH_2]_b-$ wherein a is 0 or 1, $R^a$ is selected from —OH, —NH$_2$, —NHR and —OR wherein R is a protecting group and b is an integer having a value of 0–40, and Q is moiety having the formula:

$-[CH_2]_u-[CH(R^{a'})]_t-[CH_2]_q-O-[CH_2]_r-O-[CH_2]_s-$ wherein q, r, s, t and u are the same or different and each is an integer having a value of 0–40 and $R^{a'}$ is selected from the group consisting of hydrogen, hydroxyl, a $C_1-C_{40}$ alkyl group, a $C_5-C_{40}$ aryl group, a $C_1-C_{40}$ alkoxy group, a $C_1-C_{40}$ ester group, a $C_1-C_{40}$ hydroxy-containing group, a $C_2-C_{40}$ acrylate-containing group, a $C_5-C_{40}$ alkylaryl group, —NH$_2$, —NHR and —OR, wherein R is a protecting group; and wherein the term SUPPORT is defined as an organic or an inorganic substance.

2. The reusable linker arm defined in claim 1, wherein T has the formula:

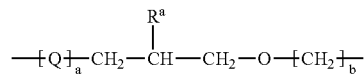

wherein q and s are the same or different and each is an integer having a value of 0–40 and r is an integer having a value of 1–200.

3. The reusable linker arm defined in claim 2, wherein q and s are the same or different and each is an integer having a value of 1–20 and r is an integer having a value of 1–150.

4. The reusable linker arm defined in claim 1, wherein T has the formula:

$-[Q]_a-CH_2-\overset{R^a}{\underset{|}{CH}}-CH_2-O-[CH_2]_b-$ wherein a is 0 or 1, $R^a$ is selected from —OH, —NH$_2$, —NR and —OR wherein R is a protecting group and b is an integer having a value of 0–40, and Q is a moiety having the formula:

$-[CH_2]_u-[CH]_t-[CH_2]_q-O-[CH_2]_r-O-[CH_2]_s-$ with $R^{a'}$ substituent wherein q, r, s, t and u are the same or different and each is an integer having a value of 0–40 and $R^{a'}$ is selected from the group consisting of hydrogen, hydroxyl, a $C_1-C_{40}$ alkyl group, a $C_5-C_{40}$ aryl group, a $C_1-C_{40}$ alkoxy group, a $C_1-C_{40}$ ester group, a $C_1-C_{40}$ hydroxy-containing group, a $C_2-C_{40}$ acrylate-containing group, a $C_5-C_{40}$ alkylaryl group, —NH$_2$, —NHR and —OR, wherein R is a protecting group.

5. The reusable linker arm defined in claim 4, wherein a is 0 and $R^a$ is —OH.

6. The reusable linker arm defined in claim 4, wherein a is 1 and $R^a$ is —NR or —OR.

7. The reusable linker arm defined in claim 4, wherein the protecting group is selected from the group consisting of acetyl, chloroacetyl, methoxyacetyl, t-butyl phenoxyacetyl, phenoxyacetyl, trityl, methoxytrityl, dimethoxytrityl (DMT), pivalyl-isobutyloxycarbonyl, t-butyldimethylsilyl, 9-phenylxanthen-9-yl (pixyl), tetrahydropyranyl, methoxytetrahydropyranyl, methoxymethyl, benzyloxymethyl, methoxyethoxymethyl, methylthiomethyl, dialkylphosphate, levulinyl, dimethylphenylsilyl, trimethylsilyl, isopropyl-dimethylsilyl, diisopropylmethylsilyl, diethylisopropylsilyl, triisopropylsilyl, benzoyl, pivaloyl, trifluoroacetyl, allyl, benzyl, o-nitrobenzyl, o-hydroxystyryldimethylsilyl, 2-oxo-1,2-diphenylethyl, allyloxycarbonyl, monomethoxymethyl, nitroveratryloxycarbonyl, fluorenylmethoxycarbonyl, 2-phenylsulfonyl-ethoxycarbony, fluorophenyl-methoxypiperidinyl and mixtures thereof.

8. The reusable linker arm defined in claim 1, wherein s is 0, q, r and u are the same or different and each is an integer having a value of 1–10, t is an integer of 1–5 and $R^a$ is hydroxyl.

9. The reusable linker arm defined in claim 1, wherein T has the formula:

$$-[Q]_a-CH_2-\overset{R^a}{\underset{|}{CH}}-CH_2-O-[CH_2]_b-$$

wherein a is 0 or 1, $R^a$ is selected from —OH, —NH$_2$, —NR and —OR wherein R is a protecting group and b is an integer having a value of 0–40.

10. The reusable linker arm defined in claim 9, wherein a is 0 and $R^a$ is —OH.

11. The reusable linker arm defined in claim 9, wherein a is 1 and $R^a$ is —NR or —OR.

12. The reusable linker arm defined in claim 4, wherein the moiety Q is unsubstituted.

13. The reusable linker arm defined in claim 4, wherein the organic moiety is substituted by at least one moiety selected from the group consisting of a $C_1$–$C_{40}$ alkyl group, a $C_5$–$C_{40}$ aryl group, a $C_1$–$C_{40}$ alkoxy group, a $C_1$–$C_{40}$ ester group, a $C_1$–$C_{40}$ hydroxy-containing group, a $C_2$–$C_{40}$ acrylate-containing group and a $C_5$–$C_{40}$ alkylaryl group.

14. The reusable linker arm defined in claim 4 wherein Q is additionally defined as having the formula:

—[CH$_2$]$_x$—C(=O)—NH—[CH$_2$]$_y$—NH—C(=O)—[CH$_2$]$_z$— wherein each of x, y and z is an integer having a value of 1–40.

15. The reusable linker arm defined in claim 1, wherein p is 0.

16. The reusable linker arm defined in claim 1, wherein $B^1$ is selected from the group consisting of hydrogen, halide, a substituted or unsubstituted $C_1$–$C_{20}$ alkyl group, a substituted or unsubstituted $C_5$–$C_{30}$ aryl group and a substituted or unsubstituted $C_5$–$C_{40}$ alkylaryl group.

17. The reusable linker arm defined in claim 1, wherein each of $R^4$, $R^5$, $R^6$ and $R^7$ is hydrogen.

18. The reusable linker arm defined in claim 1, wherein each of m and n are 1.

19. The reusable linker arm defined in claim 1, wherein each of $R^1$, $R^2$ and $R^3$ is hydrogen.

20. The reusable linker arm defined in claim 1, wherein $X^1$ and $X^2$ are both —O—.

21. The reusable linker arm defined in claim 1, wherein SUPPORT is an inorganic substance.

22. The reusable linker arm defined in claim 21, wherein the inorganic substance is selected from the group consisting of silica, glass beads, porous glass, aluminosilicates, borosilicates, metal oxides, clays and mixtures thereof.

23. The reusable linker arm defined in claim 1, wherein SUPPORT is an organic substance.

24. The reusable linker arm defined in claim 23, wherein the organic substance is a cross-linked polymer.

25. A reusable linker arm for solid support oligonucleotide synthesis consisting of the following formula:

NUCLEOSIDE-Z-O-T∼∼∼[SUPPORT]

wherein Z is selected from the group consisting of
HO$_2$C—CH$_2$—CH$_2$—(C=O)—;
HO$_2$C—CH$_2$—O—CH$_2$—(C=O)—;
HO$_2$C—(C=O)—; and $$HO-\overset{O}{\underset{\|}{C}}-(R^4R^5C)_n-X^1-\underset{R^3 \quad B^1}{\overset{R^1 \quad R^2}{\bigcirc}}-A^1$$

wherein: $R^1$, $R^2$ and $R^3$ are the same or different and are selected from the group consisting of hydrogen, halide, a substituted or unsubstituted $C_1$–$C_{20}$ alkyl group, an substituted or unsubstituted $C_5$–$C_{30}$ aryl group and a substituted or unsubstituted $C_5$–$C_{40}$ alkylaryl group;

$R^4$ and $R^5$ are the same or different and are selected from the group consisting of hydrogen, a substituted or unsubstituted $C_1$–$C_{20}$ alkyl group, an substituted or unsubstituted $C_5$–$C_{30}$ aryl group and a substituted or unsubstituted $C_5$–$C_{40}$ alkylaryl group;

$X^1$ is selected from the group consisting of —O—, —S—, —C(O)—, —S(O)$_2$—, and —N(R)—;

R is selected from the group consisting of hydrogen, a substituted or unsubstituted $C_1$–$C_{20}$ alkyl group, an substituted or unsubstituted $C_5$–$C_{30}$ aryl group and a substituted or unsubstituted $C_5$–$C_{40}$ alkylaryl group;

n is 0, 1 or 2;

and one of $A^1$ and $B^1$ is selected from the group consisting of hydrogen, halide, a substituted or unsubstituted $C_1$–$C_{20}$ alkyl group, an substituted or unsubstituted $C_5$–$C_{30}$ aryl group and a substituted or unsubstituted $C_5$–$C_{40}$ alkylaryl group and the other of $A^1$ and $B^1$ has the formula:

$$-[\bigcirc]_p-X^2(CR^6R^7)_m\overset{O}{\underset{\|}{C}}-$$

wherein p is 0 or 1;

$X^2$ is selected from the group consisting of —O—, —S—, —C(O)—, —S(O)$_2$—, and —N(R)—;

R is selected from the group consisting of hydrogen, a substituted or unsubstituted $C_1$–$C_{20}$ alkyl group, an substituted or unsubstituted $C_5$–$C_{30}$ aryl group and a substituted or unsubstituted $C_5$–$C_{40}$ alkylaryl group;

$R^6$ and $R^7$ are the same or different and are selected from the group consisting of hydrogen, a substituted or unsubstituted $C_1$–$C_{20}$ alkyl group, an substituted or unsubstituted $C_5$–$C_{30}$ aryl group and a substituted or unsubstituted $C_5$–$C_{40}$ alkylaryl group;

and T has the formula:

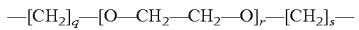

wherein q and s are the same or different and each is an integer having a value of 0–40 and r is an integer having a value of 1–200 or T has the formula:

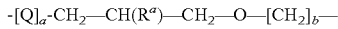

wherein a is 0 or 1, $R^a$ is selected from —OH, —$NH_2$, —NHR and —OR wherein R is a protecting group and b is an integer having a value of 0–40, and Q is moiety having the formula:

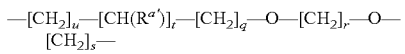

wherein q, r, s, t and u are the same or different and each is an integer having a value of 0–40 and $R^{a'}$ is selected from the group consisting of hydrogen, hydroxyl, a $C_1$–$C_{40}$ alkyl group, a $C_5$–$C_{40}$ aryl group, a $C_1$–$C_{40}$ alkoxy group, a $C_1$–$C_{40}$ ester group, a $C_1$–$C_{40}$ hydroxy-containing group, a $C_2$–$C_{40}$ acrylate-containing group, a $C_5$–$C_{40}$ alkylaryl group, —$NH_2$, —NHR and —OR, wherein R is a protecting group; and wherein the term SUPPORT is defined as an organic or an inorganic substance and wherein the term NUCLEOSIDE represents an optionally protected ribonucleosidyl or 2'-deoxyribonucleosidyl group.

26. The reusable linker arm defined in claim 25, wherein T has the formula:

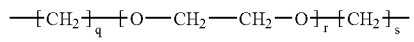

wherein q and s are the same or different and each is an integer having a value of 0–40 and r is an integer having a value of 1–200.

27. The reusable linker arm defined in claim 26, wherein q and s are the same or different and each is an integer having a value of 1–20 and r is an integer having a value of 1–150.

28. The reusable linker arm defined in claim 25, wherein T has the formula:

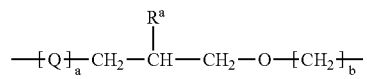

wherein a is 0 or 1, $R^a$ is selected from —OH, —$NH_2$, —NR and —OR wherein R is a protecting group and b is an integer having a value of 0–40, and Q is a moiety having the formula:

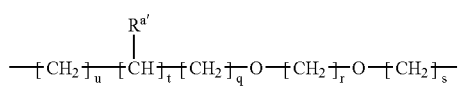

wherein q, r, s, t and u are the same or different and each is an integer having a value of 0–40 and $R^{a'}$ is selected from the group consisting of hydrogen, hydroxyl a $C_1$–$C_{40}$ alkyl group, a $C_5$–$C_{40}$ aryl group, a $C_1$–$C_{40}$ alkoxy group a $C_1$–$C_{40}$ ester group a $C_1$–$C_{40}$ hydroxy-containing group a $C_2$–$C_{40}$ acrylate-containing group, a $C_5$–$C_{40}$ alkylaryl group, —$NH_2$, —NHR and —OR, wherein R is a protecting group.

29. The reusable linker arm defined in claim 28, wherein a is 0 and $R^a$ is —OH.

30. The reusable linker arm defined in claim 28, wherein a is 1 and $R^a$ is —NR or —OR.

31. The reusable linker arm defined in claim 28, wherein the protecting group is selected from the group consisting of acetyl, chloroacetyl, methoxyacetyl, t-butyl phenoxyacetyl, trityl, methoxytrityl, dimethoxytrityl (DMT), pivalyl-isobutyloxycarbonyl, t-butyldimethylsilyl, phenoxyacetal, 9-phenylxanthen-9-yl (pixyl), tetrahydropyranyl, methoxytetrahydropyranyl, methoxymethyl, benzyloxymethyl, methoxyethoxymethyl, methylthiomethyl, dialkylphosphate, levulinyl, dimethylphenylsilyl, trimethylsilyl, isopropyl-dimethylsilyl, diisopropylmethylsilyl, diethylisopropylsilyl, triisopropylsilyl, benzoyl, pivaloyl, trifluoroacetyl, allyl, benzyl, o-nitrobenzyl, o-hydroxystyryldimethylsilyl, 2-oxo-1,2-diphenylethyl, allyloxycarbonyl, monomethoxymethyl, nitroveratryloxycarbonyl, fluorenylmethoxycarbonyl, 2-phenylsulfonyl-ethoxycarbony, fluorophenyl-methoxypiperidinyl and mixtures thereof.

32. The reusable linker arm defined in claim 28, wherein s is 0, q, r and u are the same or different and each is an integer having a value of 1–10, t is an integer of 1–5 and $R^a$ is hydroxyl.

33. The reusable linker arm defined in claim 28, wherein T has the formula:

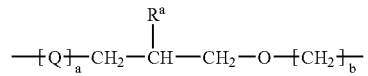

wherein a is 0 or 1, $R^a$ is selected from —OH, —$NH_2$, —NR and —OR wherein R is a protecting group and b is an integer having a value of 0–40, and Q is a moiety having the formula:

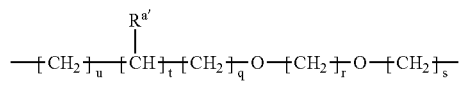

wherein q, r, s, t and u are the same or different and each is an integer having a value of 0–40 and $R^{a'}$ is selected from the group consisting of hydrogen, hydroxyl, a $C_1$–$C_{40}$ alkyl group, a $C_5$–$C_{40}$ aryl group, a $C_1$–$C_{40}$ alkoxy group, a $C_1$–$C_{40}$ ester group hydroxy-containing group, a $C_2$–$C_{40}$ acrylate-containing group, a $C_5$–$C_{40}$ alkylaryl group, —$NH_2$, —NHR and —OR, wherein R is a protecting group.

34. The reusable linker arm defined in claim 33, wherein a is 0 and $R^a$ is —OH.

35. The reusable linker arm defined in claim 33, wherein a is 1 and $R^a$ is —NHR or —OR.

36. The reusable linker arm defined in claim 33, wherein the organic moiety is unsubstituted.

37. The reusable linker arm defined in claim 33, wherein the moiety Q is substituted by at least one moiety selected from the group consisting of a $C_1$–$C_{40}$ alkyl group, a $C_5$–$C_{40}$ aryl group, a $C_1$–$C_{40}$ alkoxy group, a $C_1$–$C_{40}$ ester group, a $C_1$–$C_{40}$ hydroxy group, a $C_2$–$C_{40}$ acrylate group and a $C_5$–$C_{40}$ alkylaryl group.

38. The reusable linker arm defined in claim 4 wherein Q is additionally defined as having the formula:

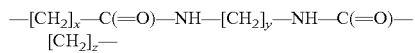

wherein each of x, y and z is an integer having a value of 1–40.

39. The reusable linker arm defined in claim 25, wherein p is 0.

40. The reusable linker arm defined in claim 25, wherein $B^1$ is selected from the group consisting of hydrogen, halide, a substituted or unsubstituted $C_1$–$C_{20}$ alkyl group, a substituted or unsubstituted $C_5$–$C_{30}$ aryl group and a substituted or unsubstituted $C_5$–$C_{40}$ alkylaryl group.

41. The reusable linker arm defined in claim 25, wherein each of $R^4$, $R^5$, $R^6$ and $R^7$ is hydrogen.

42. The reusable linker arm defined in claim 25, wherein each of m and n are 1.

43. The reusable linker arm defined in claim 25, wherein each of $R^1$, $R^2$ and $R^3$ is hydrogen.

44. The reusable linker arm defined in claim 25, wherein $X^1$ and $X^2$ are both —O—.

45. The reusable linker arm defined in claim 25, wherein SUPPORT is an inorganic substance.

46. The reusable linker arm defined in claim 45, wherein the inorganic substance is selected from the group consisting of silica, glass beads, porous glass, aluminosilicates, borosilicates, metal oxides, clays and mixtures thereof.

47. The reusable linker arm defined in claim 25, wherein SUPPORT is an organic substance.

48. The reusable linker arm defined in claim 47, wherein the organic substance is a cross-linked polymer.

49. The reusable linker arm defined in claim 25, wherein NUCLEOSIDE is a moiety selected from one of the following formulae:

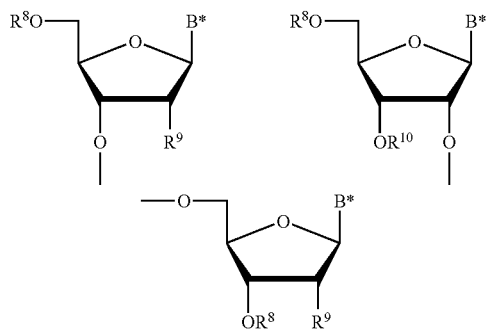

wherein $R^8$ and $R^{10}$ are hydrogen or a protecting group, $R^9$ is hydrogen or —$OR^{11}$ wherein $R^{11}$ protecting group, and B* is a nucleic acid base.

50. A process for production of a reusable linker arm for oligonucleotide synthesis having the following formula:

wherein Z is selected from the group consisting of:

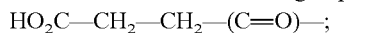
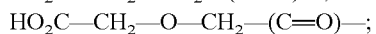
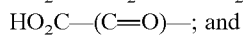

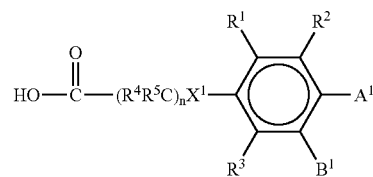

wherein: $R^1$, $R^2$ and $R^3$ are the same or different and are selected from the group consisting of hydrogen, halide, a substituted or unsubstituted $C_1$–$C_{20}$ alkyl group, an substituted or unsubstituted $C_5$–$C_{30}$ aryl group and a substituted or unsubstituted $C_5$–$C_{40}$ alkylaryl group;

$R^4$ and $R^5$ are the same or different and are selected from the group consisting of hydrogen, a substituted or unsubstituted $C_1$–$C_{20}$ alkyl group, an substituted or unsubstituted $C_5$–$C_{30}$ aryl group and a substituted or unsubstituted $C_5$–$C_{40}$ alkylaryl group;

$X^1$ is selected from the group consisting of —O—, —S—, —C(O)—, —S(O)$_2$—, and —N(R)—;

R is selected from the group consisting of hydrogen, a substituted or unsubstituted $C_1$–$C_{20}$ alkyl group, an substituted or unsubstituted $C_5$–$C_{30}$ aryl group and a substituted or unsubstituted $C_5$–$C_{40}$ alkylaryl group;

n is 0, 1 or 2;

and one of $A^1$ and $B^1$ is selected from the group consisting of hydrogen, halide, a substituted or unsubstituted $C_1$–$C_{20}$ alkyl group, an substituted or unsubstituted $C_5$–$C_{30}$ aryl group and a substituted or unsubstituted $C_5$–$C_{40}$ alkylaryl group and the other of $A^1$ and $B^1$ has the formula:

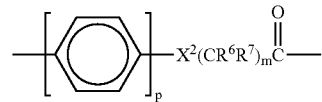

wherein p is 0 or 1;

$X^2$ is selected from the group consisting of —O—, —S—, —C(O)—, —S(O)$_2$—, and —N(R)—;

R is selected from the group consisting of hydrogen, a substituted or unsubstituted $C_1$–$C_{20}$ alkyl group, an substituted or unsubstituted $C_5$–$C_{30}$ aryl group and a substituted or unsubstituted $C_5$–$C_{40}$ alkylaryl group;

$R^6$ and $R^7$ are the same or different and are selected from the group consisting of hydrogen, a substituted or unsubstituted $C_1$–$C_{20}$ alkyl group, an substituted or unsubstituted $C_5$–$C_{30}$ aryl group and a substituted or unsubstituted $C_5$–$C_{40}$ alkylaryl group;

and T has the formula:

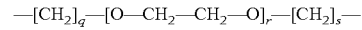

wherein q and s are the same or different and each is an integer having a value of 0–40 and r is an integer having a value of 1–200 or T has the formula:

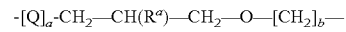

wherein a is 0 or 1, $R^a$ is selected from —OH, —$NH_2$, —NHR and —OR wherein R is a protecting group and b is an integer having a value of 0–40, and Q is moiety having the formula:

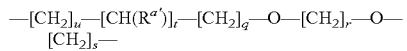

wherein q, r, s, t and u are the same or different and each is an integer having a value of 0–40 and $R^{a'}$ is selected from the group consisting of hydrogen, hydroxyl, a $C_1$–$C_{40}$ alkyl group, a $C_5$–$C_{40}$ aryl group, a $C_1$–$C_{40}$ alkoxy group, a $C_1$–$C_{40}$ ester group, a $C_1$–$C_{40}$ hydroxy-containing group, a $C_2$–$C_{40}$ acrylate-containing group, a $C_5$–$C_{40}$ alkylaryl group, —$NH_2$, —NHR and —OR, wherein R is a protecting group, the process comprising a sequence of steps or reacting together the compounds of the Formulae I and II

   (I)

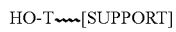   (II)

in the presence of an activating agent; and wherein Z ands T are as defined above; and wherein the term SUPPORT is defined as an organic or an inorganic substance.

51. The process defined in claim 50, wherein the moiety Q is unsubstituted.

52. The process defined in claim 50, wherein the moiety Q is substituted by at least one moiety selected from the group consisting of a $C_1$–$C_{40}$ alkyl group, a $C_5$–$C_{40}$ aryl group, a $C_1$–$C_{40}$ alkoxy group, a $C_1$–$C_{40}$ ester group, a $C_1$–$C_{40}$ hydroxy-containing group, a $C_2$–$C_{40}$ acrylate-containing group and a $C_5$–$C_{40}$ alkylaryl group.

53. The process defined in claim 50, wherein T has the formula:

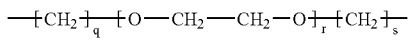

wherein q and s are the same or different and each is an integer having a value of 0–40 and r is an integer having a value of 1–200.

54. The process defined in claim 53, wherein q and s are the same or different and each is an integer having a value of 1–20 and r is an integer having a value of 1–150.

55. The process defined in claim 50, wherein T has the formula:

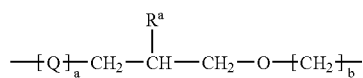

wherein a is 0 or 1, $R^a$ is selected from —OH, —$NH_2$, —NHR and —OR wherein R is a protecting group and b is an integer having a value of 0–40 and Q is a moiety having the formula:

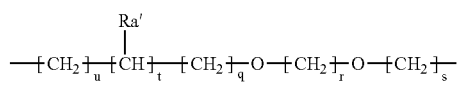

wherein q r s, t and u are the same or different and each is an integer having a value of 0–40 and $R^{a'}$ is selected from the group consisting of hydrogen, hydroxyl, a $C_1$–$C_{40}$ alkyl group, a $C_5$–$C_{40}$ aryl group, a $C_1$–$C_{40}$ alkoxy group, a $C_1$–$C_{40}$ ester group, a $C_1$–$C_{40}$ hydroxy-containing group, a $C_2$–$C_{40}$ acrylate-containing group, a $C_5$–$C_{40}$ alkylaryl group, $NH_2$, —NHR and —OR, wherein R is a protecting group.

56. The reusable linker arm defined in claim 55, wherein a is 0 and $R^a$ is —OH.

57. The reusable linker arm defined in claim 55, wherein a is 1 and $R^a$ is —NR or —OR.

58. The process defined in claim 55, wherein the protecting group is selected from the group consisting of acetyl, chloroacetyl, methoxyacetyl, t-butyl phenoxyacetyl, trityl, methoxytrityl, dimethoxytrityl (DMT), pivalyl-isobutyloxycarbonyl, t-butyldimethylsilyl, phenoxyacetal, 9-phenylxanthen-9-yl (pixyl), tetrahydropyranyl, methoxytetrahydropyranyl, methoxymethyl, benzyloxymethyl, methoxyethoxymethyl, methylthiomethyl, dialkylphosphate, levulinyl, dimethylphenylsilyl, trimethylsilyl, isopropyl-dimethylsilyl, diisopropylmethylsilyl, diethylisopropylsilyl, triisopropylsilyl, benzoyl, pivaloyl, trifluoroacetyl, allyl, benzyl, o-nitrobenzyl, o-hydroxystyryldimethylsilyl, 2-oxo-1,2-diphenylethyl, allyloxycarbonyl, monomethoxymethyl, nitroveratryloxycarbonyl, fluorenylmethoxycarbonyl, 2-phenylsulfonyl-ethoxycarbony, fluorophenyl-methoxypiperidinyl and mixtures thereof.

59. The process defined in claim 50, wherein p is 0.

60. The process defined in claim 50, wherein $B^1$ is selected from the group consisting of hydrogen, halide, a substituted or unsubstituted $C_1$–$C_{20}$ alkyl group, a substituted or unsubstituted $C_5$–$C_{30}$ aryl group and a substituted or unsubstituted $C_5$–$C_{40}$ alkylaryl group.

61. The process defined in claim 50, wherein each of $R^4$, $R^5$, $R^6$ and $R^7$ is hydrogen.

62. The process defined in claim 50, wherein each of m and n are 1.

63. The process defined in claim 50, wherein each of $R^1$, $R^2$ and $R^3$ is hydrogen.

64. The process defined in claim 50, wherein $X^1$ and $X^2$ are both —O—.

65. The process defined in claim 50, wherein SUPPORT is an inorganic substance.

66. The process defined in claim 65, wherein the inorganic substance is selected from the group consisting of silica, glass beads, porous glass, aluminosilicates, borosilicates, metal oxides, clays and mixtures thereof.

67. The process defined in claim 50, wherein SUPPORT is an organic substance.

68. The process defined in claim 67, wherein the organic substance is a cross-linked polymer.

69. The process defined in claim 50, wherein the activating agent is selected from the group consisting of an acid chloride; an active ester; an active hydroxylamine ester; acid anhydride and mixed anhydride.

70. The process defined in claim 50, wherein the activating agent is selected from the group consisting of one or more arylsulfonyl chlorides; active arylsulfonyl esters; 2-ethoxy-1-(ethoxycarbonyl)-1,2-dihydroquinoline (EEDQ); one or more acyl carbonates one or more 1,1'-(carbonyldioxybenzotriazoles); chlorotrimethylsilane one or more carbodiimides either alone or in combination with auxiliary nucleophiles and/or catalysts; or uronium salts a catalyst or phosphonium salts or mixtures thereof.

71. A process for production of a reusable linker arm for oligonucleotide synthesis having the following formula:

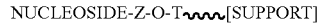

wherein Z is selected from the group consisting of:
  $HO_2C$—$CH_2$—$CH_2$—(C=O)—;
  $HO_2C$—$CH_2$—O—$CH_2$—(C=O)—;
  $HO_2C$—(C=O)—; and

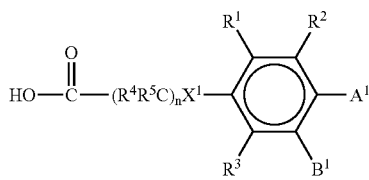

wherein: $R^1$, $R^2$ and $R^3$ are the same or different and are selected from the group consisting of hydrogen, halide, a substituted or unsubstituted $C_1$–$C_{20}$ alkyl group, an substituted or unsubstituted $C_5$–$C_{30}$ aryl group and a substituted or unsubstituted $C_5$–$C_{40}$ alkylaryl group;

$R^4$ and $R^5$ are the same or different and are selected from the group consisting of hydrogen, a substituted or unsubstituted $C_1$–$C_{20}$ alkyl group, an substituted or unsubstituted $C_5$–$C_{30}$ aryl group and a substituted or unsubstituted $C_5$–$C_{40}$ alkylaryl group;

$X^1$ is selected from the group consisting of —O—, —S—, —C(O)—, —S(O)$_2$—, and —N(R)—;

R is selected from the group consisting of hydrogen, a substituted or unsubstituted $C_1$–$C_{20}$ alkyl group, an substituted or unsubstituted $C_5$–$C_{30}$ aryl group and a substituted or unsubstituted $C_5$–$C_{40}$ alkylaryl group;

n is 0, 1 or 2;

and one of $A^1$ and $B^1$ is selected from the group consisting of hydrogen, halide, a substituted or unsubstituted $C_1$–$C_{20}$ alkyl group, an substituted or unsubstituted $C_5$–$C_{30}$ aryl group and a substituted or unsubstituted $C_5$–$C_{40}$ alkylaryl group and the other of $A^1$ and $B^1$ has the formula:

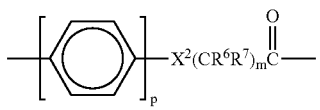

wherein p is 0 or 1;

$X^2$ is selected from the group consisting of —O—, —S—, —C(O)—, —S(O)$_2$—, and —N(R)—;

R is selected from the group consisting of hydrogen, a substituted or unsubstituted $C_1$–$C_{20}$ alkyl group, an substituted or unsubstituted $C_5$–$C_{30}$ aryl group and a substituted or unsubstituted $C_5$–$C_{40}$ alkylaryl group;

$R^6$ and $R^7$ are the same or different and are selected from the group consisting of hydrogen, a substituted or unsubstituted $C_1$–$C_{20}$ alkyl group, an substituted or unsubstituted $C_5$–$C_{30}$ aryl group and a substituted or unsubstituted $C_5$–$C_{40}$ alkylaryl group;

and T has the formula:

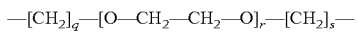

wherein q and s are the same or different and each is an integer having a value of 0–40 and r is an integer having a value of 1–200 or T has the formula:

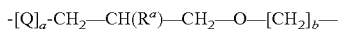

wherein a is 0 or 1, $R^a$ is selected from —OH, —NH$_2$, —NHR and —OR wherein R is a protecting group and b is an integer having a value of 0–40, and Q is moiety having the formula:

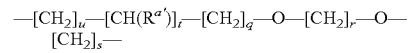

wherein q, r, s, t and u are the same or different and each is an integer having a value of 0–40 and $R^{a'}$ is selected from the group consisting of hydrogen, hydroxyl, a $C_1$–$C_{40}$ alkyl group, a $C_5$–$C_{40}$ aryl group, a $C_1$–$C_{40}$ alkoxy group, a $C_1$–$C_{40}$ ester group, a $C_1$–$C_{40}$ hydroxy-containing group, a $C_2$–$C_{40}$ acrylate-containing group, a $C_5$–$C_{40}$ alkylaryl group, —NH$_2$, —NHR and —OR, wherein R is a protecting group, the process comprising a sequence of steps or reacting together the compounds having Formulae I, II and III in the presence of an activating agent

wherein Z ands T are as defined above and;

wherein the term SUPPORT is defined as an organic or an inorganic substance; and wherein the term NUCLEOSIDE represents an optionally protected ribonucleosidyl or 2'-deoxyribonucleosidyl group;

with the proviso that said compounds are reacted in the pairs I+II, or I+III, prior to the coupling of the resultant intermediate product with the remaining compound.

72. The process defined in claim 71, wherein the moiety Q is unsubstituted.

73. The process defined in claim 71, wherein the moiety Q is substituted by at least one moiety selected from the group consisting of a $C_1$–$C_{40}$ alkyl group, a $C_5$–$C_{40}$ aryl group, a $C_1$–$C_{40}$ alkoxy group, a $C_1$–$C_{40}$ ester group, a $C_1$–$C_{40}$ hydroxy group, a $C_2$–$C_{40}$ acrylate group and a $C_5$–$C_{40}$ alkylaryl group.

74. The process defined in claim 71, wherein T has the formula:

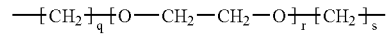

wherein q and s are the same or different and each is an integer having a value of 0–40 and r is an integer having a value of 1–200.

75. The process defined in claim 74, wherein q and s are the same or different and each is an integer having a value of 1–20 and r is an integer having a value of 1–150.

76. The process defined in claim 71, wherein T has the formula:

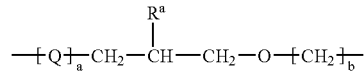

wherein a is 0 or 1, Q is an organic moiety, $R^a$ is selected from —OH, —NH$_2$, —NHR and —OR wherein R is a protecting group and b is an integer having a value of 0–40, and Q is a moiety having the formula:

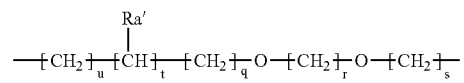

wherein q, r, s, t and u are the same or different and each is an integer having a value of 0–40 and $R^{a'}$ is selected from the group consisting of hydrogen, hydroxyl, a $C_1$–$C_{40}$ alkyl group, a $C_5$–$C_{40}$ aryl group, a $C_1$–$C_{40}$ alkoxy group, a $C_1$–$C_{40}$ ester group, a $C_1$–$C_{40}$ hydroxy-containing group, a $C_2$–$C_{40}$ acrylate-containing group, a $C_5$–$C_{40}$ alkylaryl group, —$NH_2$, —NHR and —OR wherein R is a protecting group.

77. The reusable linker arm defined in claim 76, wherein a is 0 and $R^a$ is —OH.

78. The reusable linker arm defined in claim 76, wherein a is 1 and $R^a$ is —NR or —OR.

79. The process defined in claim 76, wherein the protecting group is selected from the group consisting of acetyl, chloroacetyl, methoxyacetyl, t-butyl phenoxyacetyl, trityl, methoxytrityl, dimethoxytrityl (DMT), pivalyl-isobutyloxycarbonyl, t-butyldimethylsilyl, phenoxyacetal, 9-phenylxanthen-9-yl (pixyl), tetrahydropyranyl, methoxytetrahydropyranyl, methoxymethyl, benzyloxymethyl, methoxyethoxymethyl, methylthiomethyl, dialkylphosphate, levulinyl, dimethylphenylsilyl, trimethylsilyl, isopropyl-dimethylsilyl, diisopropylmethylsilyl, diethylisopropylsilyl, triisopropylsilyl, benzoyl, pivaloyl, trifluoroacetyl, allyl, benzyl, o-nitrobenzyl, o-hydroxystyryldimethylsilyl, 2-oxo-1,2-diphenylethyl, allyloxycarbonyl, monomethoxymethyl, nitroveratryloxycarbonyl, fluorenylmethoxycarbonyl, 2-phenylsulfonyl-ethoxycarbony, fluorophenyl-methoxypiperidinyl and mixtures thereof.

80. The process defined in claim 71, wherein p is 0.

81. The process defined in claim 71, wherein $B^1$ is selected from the group consisting of hydrogen, halide, a substituted or unsubstituted $C_1$–$C_{20}$ alkyl group, a substituted or unsubstituted $C_5$–$C_{30}$ aryl group and a substituted or unsubstituted $C_5$–$C_{40}$ alkylaryl group.

82. The process defined in claim 71, wherein each of $R^4$, $R^5$ $R^6$ and $R^7$ is hydrogen.

83. The process defined in claim 71, wherein each of m and n are 1.

84. The process defined in claim 71, wherein each of $R^1$, $R^2$ and $R^3$ is hydrogen.

85. The process defined in claim 71, wherein $X^1$ and $X^2$ are both —O—.

86. The process defined in claim 71, wherein SUPPORT is an inorganic substance.

87. The process defined in claim 86, wherein the inorganic substance is selected from the group consisting of silica, glass beads, porous glass, aluminosilicates, borosilicates, metal oxides, clays and mixtures thereof.

88. The process defined in claim 71, wherein SUPPORT is an organic substance.

89. The process defined in claim 88, wherein the organic substance is a cross-linked polymer.

90. The process defined in claim 71, wherein the activating agent comprises at least one member selected from the group consisting of an acid chloride; an active ester; an active hydroxylamine ester; acid anhydride and mixed acid anhydride.

91. The process defined in claim 71, wherein the activating agent is selected from the group consisting of one or more arylsulfonyl chlorides, one or more active arylsulfonyl esters, 2-ethoxy-1-(ethoxycarbonyl)-1,2-dihydroquinoline (EEDQ), one or more acyl carbonates, one or more 1,1'-(carbonyldioxy)dibenzotriazoles, chlorotrimethylsilane, and one or more carbodiimides; alone or in combination with a catalyst, one or more uronium salts, or one or more phosphonium salts; or mixtures thereof, or mixtures thereof with auxiliary nucleophiles.

92. The process defined in claim 71, wherein NUCLEOSIDE is a moiety selected from one of the following formulae:

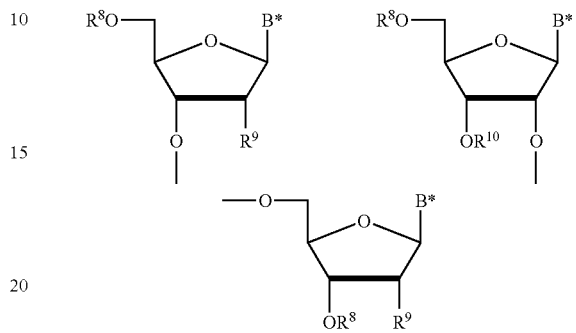

wherein $R^8$ and $R^{10}$ are the same or different and are hydrogen or a protecting group, $R^9$ is hydrogen or —$OR^{11}$ wherein $R^{11}$ is hydrogen or a protecting group, and B* is a nucleic acid base.

93. The process defined in claim 71, wherein the compounds of Formulae I and II are initially reacted to form a conjugate which is reacted with the compound of Formula III.

94. The process defined in claim 71, wherein compounds of Formulae I and III are initially reacted to form a conjugate which is reacted with the compound of Formula II.

95. A process for producing an oligonucleotide having a desired sequence comprising the steps of:
  (i) reacting a linker arm having the formula:

NUCLEOSIDE-Z-O-T~~~[SUPPORT]

wherein Z is selected from the group consisting of:
    $HO_2C$—$CH_2$—$CH_2$—(C=O)—;
    $HO_2C$—$CH_2$—O—$CH_2$—(C=O)—;
    $HO_2C$—(C=O)—; and

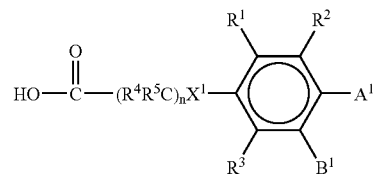

wherein: $R^1$, $R^2$ and $R^3$ are the same or different and are selected from the group consisting of hydrogen, halide, a substituted or unsubstituted $C_1$–$C_{20}$ alkyl group, an substituted or unsubstituted $C_5$–$C_{30}$ aryl group and a substituted or unsubstituted $C_5$–$C_{40}$ alkylaryl group;
  $R^4$ and $R^5$ are the same or different and are selected from the group consisting of hydrogen, a substituted or unsubstituted $C_1$–$C_{20}$ alkyl group, an substituted or unsubstituted $C_1$–$C_{30}$ aryl group and a substituted or unsubstituted $C_5$–$C_{40}$ alkylaryl group;
  $X^1$ is selected from the group consisting of —O—, —S—, —C(O)—, —$S(O)_2$—, and —N(R)—;
  R is selected from the group consisting of hydrogen, a substituted or unsubstituted $C_1$–$C_{20}$ alkyl group, an substituted or unsubstituted $C_5$–$C_{30}$ aryl group and a substituted or unsubstituted $C_5$–$C_{40}$ alkylaryl group;

n is 0, 1 or 2;

and one of $A^1$ and $B^1$ is selected from the group consisting of hydrogen, halide, a substituted or unsubstituted $C_1$–$C_{20}$ alkyl group, an substituted or unsubstituted $C_5$–$C_{30}$ aryl group and a substituted or unsubstituted $C_5$–$C_{40}$ alkylaryl group and the other of $A^1$ and $B^1$ has the formula:

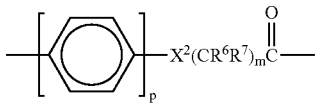

wherein p is 0 or 1;

$X^2$ is selected from the group consisting of —O—, —S—, —C(O)—, —S(O)$_2$—, and —N(R)—;

R is selected from the group consisting of hydrogen, a substituted or unsubstituted $C_1$–$C_{20}$ alkyl group, an substituted or unsubstituted $C_5$–$C_{30}$ aryl group and a substituted or unsubstituted $C_5$–$C_{40}$ alkylaryl group;

$R^6$ and $R^7$ are the same or different and are selected from the group consisting of hydrogen, a substituted or unsubstituted $C_1$–$C_{20}$ alkyl group, an substituted or unsubstituted $C_5$–$C_{30}$ aryl group and a substituted or unsubstituted $C_5$–$C_{40}$ alkylaryl group;

and T has the formula:

—[CH$_2$]$_q$—[O—CH$_2$—CH$_2$—O]$_r$[CH$_2$]$_s$— wherein q and s are the same or different and each is an integer having a value of 0–40 and r is an integer having a value of 1–200 or T has the formula:

-[Q]$_a$-CH$_2$—CH(R$^a$)—CH$_2$—O—[CH$_2$]$_b$— wherein a is 0 or 1, $R^a$ is selected from —OH, —NH$_2$, —NHR and —OR wherein R is a protecting group and b is an integer having a value of 0–40, and Q is moiety having the formula:

—[CH$_2$]$_u$—[CH(R$^{a'}$)]$_t$—[CH$_2$]$_q$—O—[CH$_2$]$_r$—O—[CH$_2$]$_s$— wherein q, r, s, t and u are the same or different and each is an integer having a value of 0–40 and $R^{a'}$ is selected from the group consisting of hydrogen, hydroxyl, a $C_1$–$C_{40}$ alkyl group, a $C_5$–$C_{40}$ aryl group, a $C_1$–$C_{40}$ alkoxy group, a $C_1$–$C_{40}$ ester group, a $C_1$–$C_{40}$ hydroxy-containing group, a $C_2$–$C_{40}$ acrylate-containing group, a $C_5$–$C_{40}$ alkylaryl group, —NH$_2$, —NHR and —OR, wherein R is a protecting group, with at least one activated nucleotide monomer until an oligonucleotide having the desired sequence is produced;

(ii) cleaving the oligonucleotide having the desired sequence to produce a free oligonucleotide having the desired sequence; and a used linker arm; and (iii) isolating the used linker arm; and wherein the term SUPPORT is defined as an organic or an inorganic substance; and wherein the term NUCLEOSIDE represents an optionally protected ribonucleosidyl or 2'-deoxyribonucleosidyl group.

96. The process defined in claim 95, wherein the used linker arm produced in Step (ii) has the formula:

Z-O-T∿∿[SUPPORT]

wherein Z, T and SUPPORT are as defined in claim 95.

97. The process defined in claim 95, wherein Step (iii) further comprises the additional step of converting the used linked arm to a linker arm having the formula:

NUCLEOSIDE-Z-O-T∿∿[SUPPORT]

wherein Z, T, NUCLEOSIDE and SUPPORT are as defined in claim 95; and wherein the additional step comprises contacting the used linker arm with an activating agent in the presence of an appropriately protected NUCLEOSIDE.

* * * * *